US010258354B2

(12) United States Patent
Turjman et al.

(10) Patent No.: US 10,258,354 B2
(45) Date of Patent: Apr. 16, 2019

(54) POST-CONDITIONING SUCTION CATHETER APPARATUS AND METHODS

(71) Applicant: Cognition Medical Corp, Cambridge, MA (US)

(72) Inventors: Alexis S. Turjman, Cambridge, MA (US); Elad I. Levy, Amherst, NY (US); Jonah G. Bernstein, Brighton, MA (US)

(73) Assignee: Cognition Medical Corp, Atlanta, GA (US)

( * ) Notice: Subject to any disclaimer, the term of this patent is extended or adjusted under 35 U.S.C. 154(b) by 556 days.

(21) Appl. No.: 14/979,310

(22) Filed: Dec. 22, 2015

(65) Prior Publication Data

US 2016/0174995 A1 Jun. 23, 2016

Related U.S. Application Data

(60) Provisional application No. 62/095,364, filed on Dec. 22, 2014.

(51) Int. Cl.
*A61B 17/22* (2006.01)

(52) U.S. Cl.
CPC .... *A61B 17/22* (2013.01); *A61B 2017/22062* (2013.01); *A61B 2017/22067* (2013.01); *A61B 2017/22069* (2013.01); *A61B 2017/22079* (2013.01); *A61B 2217/005* (2013.01)

(58) Field of Classification Search
CPC .......... A61B 2017/22051; A61B 2017/22069; A61B 2017/22067; A61B 2017/22079; A61B 17/22
See application file for complete search history.

(56) References Cited

U.S. PATENT DOCUMENTS

2006/0241566 A1* 10/2006 Moon .............. A61B 17/22031
604/540
2014/0155980 A1 6/2014 Turjman et al.
2015/0230820 A1 8/2015 Turjman et al.

FOREIGN PATENT DOCUMENTS

WO WO 2014/008460 1/2014

* cited by examiner

*Primary Examiner* — Ashley L Fishback
(74) *Attorney, Agent, or Firm* — Levine Bagade Han LLP

(57) ABSTRACT

A balloon suction catheter may be used to remove clots and increase blood flow to obstructed vessels such as a cerebral artery in a stroke patient. The catheter may be used to apply suction on the clot while providing flow arrest, embolic protection, and optionally flow reversal. The same catheter may also be used to provide for a flow modulation procedure known as post-conditioning to potentially reduce any damage from the sudden reintroduction of blood flow reperfusion injury.

14 Claims, 23 Drawing Sheets

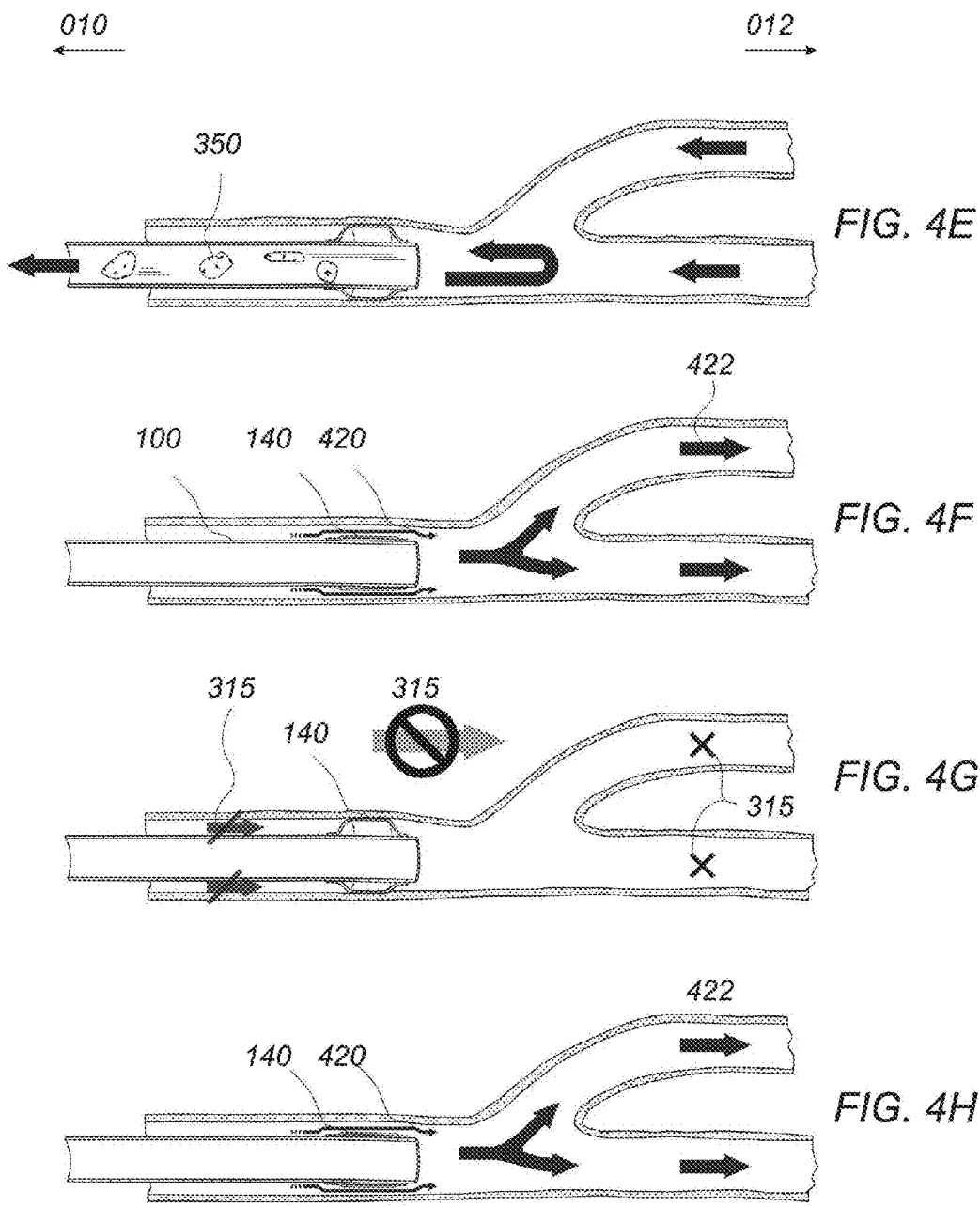

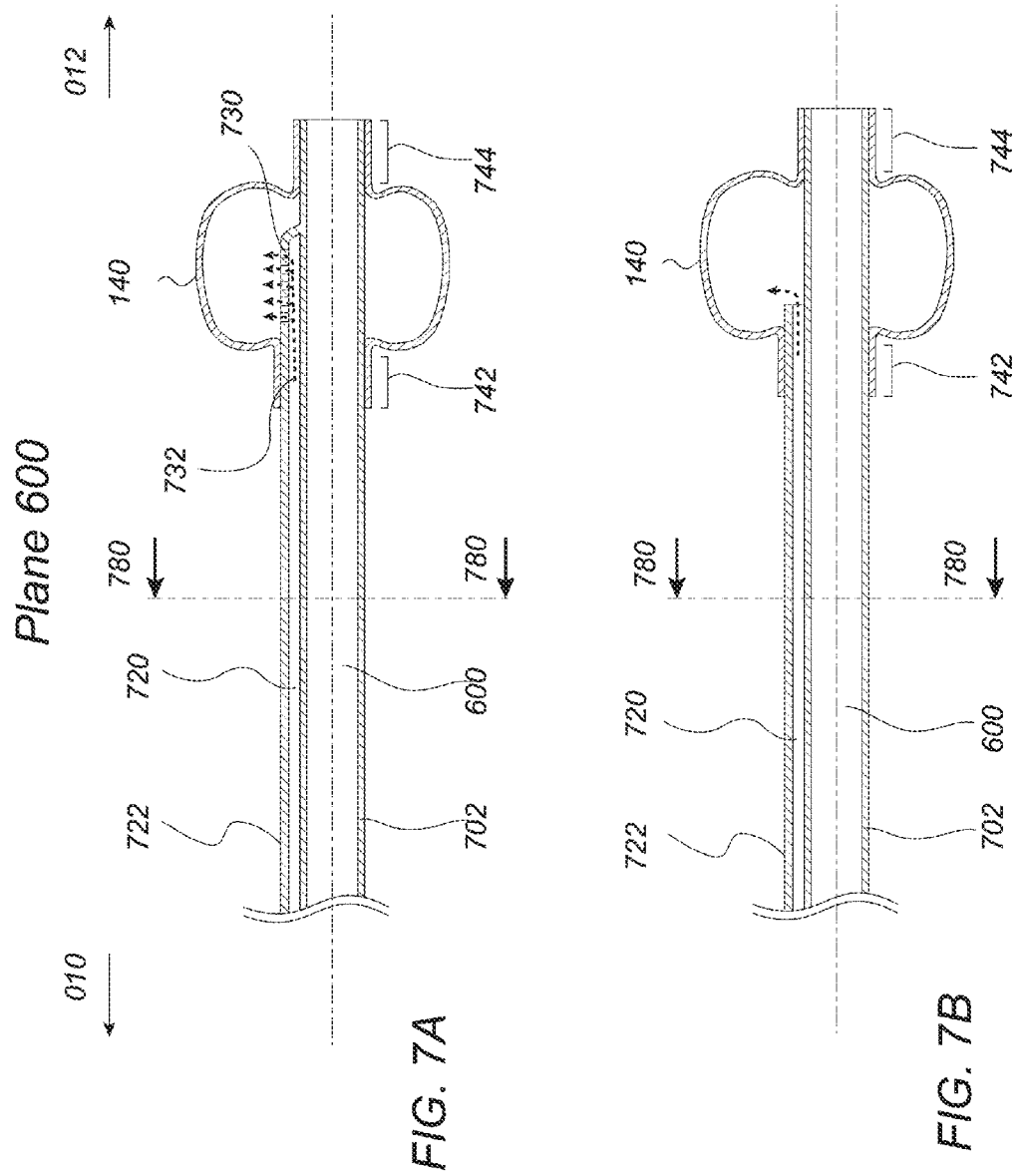

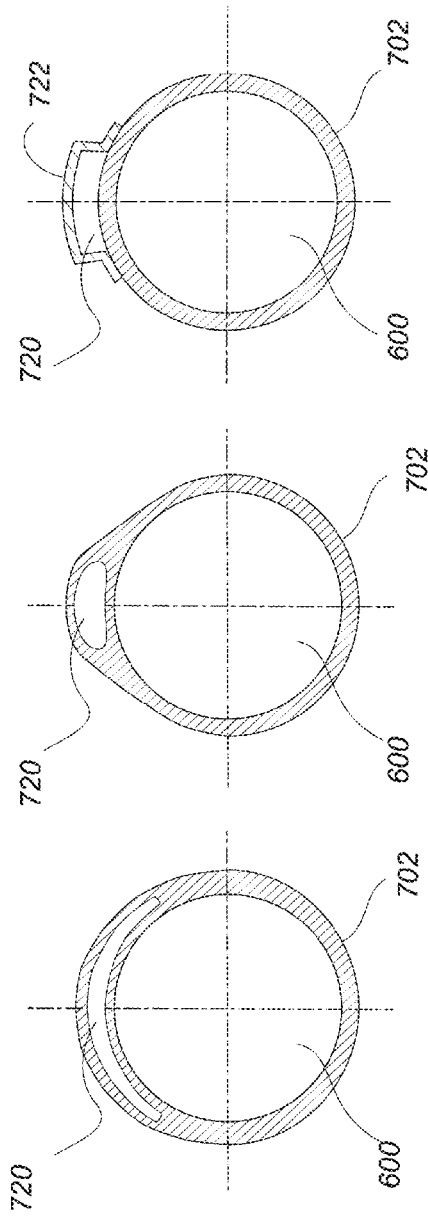

POST-CONDITIONING SUCTION CATHETER APPARATUS AND METHODS

CROSS-REFERENCE TO RELATED APPLICATIONS

This application claims the benefit of priority to U.S. Prov. App. No. 62/095,364 filed Dec. 22, 2014, which is incorporated herein by reference in its entirety.

FIELD OF THE INVENTION

The invention relates generally to methods, devices, and systems for treating vascular disorders. More specifically, the present disclosure relates to methods, devices, and systems for restoring blood flow by, e.g., removing blood clots, and/or modulating post-reperfusion blood flow.

BACKGROUND OF THE INVENTION

Ischemia, the restriction of blood supply to tissue, may result in tissue damage in a process known as ischemic cascade. Damage includes, but is not limited to, shortage of metabolic requirements (i.e., oxygen and glucose), build-up of metabolic waste products, inability to maintain cell membranes, mitochondrial damage, and eventual leakage of autolysing proteolytic enzymes into the cell and surrounding tissues. Brain ischemia may be chronic, e.g., leading to vascular dementia, or acute, e.g., causing a stroke. A stroke is the rapid decline of brain function due to a disturbance in the supply of blood to the brain caused by an obstruction or hemorrhage in a blood vessel. Obstructions encompass emboli, thrombi, and/or thromboemboli. An ischemic stroke is a stroke in which a blood vessel is restricted or occluded by an obstruction.

Ischemic stroke is the fourth leading cause of death in the United States, affecting over 795,000 patients per year and costing tens of billions of healthcare dollars. See, e.g., Dariush Mozaffarian et al., "Heart Disease and Stroke Statistics—2015 Update: A Report from the American Heart Association," *Circulation* 2015; 131:e29-e322. Furthermore, patients who survive an ischemic stroke often require rehabilitation and management of symptoms including loss of brain function, motor skills, and memory. The extent of infarction (i.e., destruction of brain tissue) correlates with the extent of these lingering effects of the stroke and the mortality rate.

Of the existing treatment options for ischemic stroke, an older method, but still the primary method used in the United States, is to treat the clot with a clot-dissolving enzyme known as tissue plasminogen activator ("tPA"). The use of tPA has two primary drawbacks. First, tPA has limited effectiveness, in both dissolving clots and providing overall benefits for the patients. Many patients do not qualify for tPA treatment because they do not arrive at the hospital within the effective time window of approximately 4.5 hours after the onset of stroke. Even when used within that window, tPA achieves only a limited decrease in the overall mortality rate. Second, tPA may present adverse effects, such as serious internal bleeding. See, e.g., Götz Thomalla et al., "Two Tales: Hemorrhagic Transformation But Not Parenchymal Hemorrhage After Thrombolysis Is Related to Severity and Duration of Ischemia: MRI Study of Acute Stroke Patients Treated with Intravenous Tissue Plasminogen Activator Within 6 Hours," 38(2) *Stroke* 313-18 (2007).

A newer method to treat ischemic stroke is mechanical thrombectomy, in which a device physically engages with a clot and is used to drag the clot out of the body. Usually, an operator, e.g., an interventional neuroradiologist or neurosurgeon, first establishes a path for the thrombectomy device to reach a clot in the cerebral vasculature by inserting an initial glidewire and guiding catheter into an artery in a lower region of the body, such as the femoral artery. Then, the operator steers the glidewire and guiding catheter to the skull base. The glidewire is removed and a combination of guidewire inside a microcatheter (optionally inside an intermediate catheter) is navigated through the guiding catheter and the arteries leading up to the obstruction and just past (i.e., distal to) the position of the obstruction or clot. Favoring whichever path poses least resistance, the guidewire passes either between the clot and the blood vessel wall or through the clot. The operator inserts a microcatheter over the initial guidewire to follow its path until reaching a position distal to the clot. The initial guidewire may be removed and replaced with a new guidewire (hereinafter "pushwire" to differentiate from an initial guidewire). This pushwire has a thrombectomy device attached to its distal end to engage with the obstruction and/or clot.

Currently, the most successful class of thrombectomy devices is based on neurovascular stent technology. Like stents, which are self-expandable and generally cylindrical, these devices tend to expand to the shape of the blood vessel walls. Thrombectomy devices may comprise thin metal struts arranged to create a cell pattern. During device expansion, a clot may become enmeshed in the cells and compressed against a blood vessel wall. At this point, blood flow may be partially or fully restored in the vessel, thus relieving ischemia.

Recently, the publication of the results of 5 landmark studies in the New England Journal of Medicine has shifted the paradigm of clinical management of ischemic stroke. The two-arm randomized trials, namely, "MR CLEAN", "SWIFT PRIME", "REVASCAT", "ESCAPE" and "EXTEND-IA", show that a combination of drug and device-based endovascular thrombectomy procedure is superior than a purely pharmacological approach. See, e.g., Jeffrey L. Saver et al., "Stent-Retriever Thrombectomy after Intravenous t-PA vs. t-PA Alone in Stroke." 372 *New England Journal of Medicine* 2285-2295 (2015). The studies have established a significant improvement in neurological outcomes in patients treated with tPA and strent retrievers compared to the group treated with tPA alone. These findings have spurred a wave of interest toward endovascular devices that can clear obstruction in the cerebrovasculature.

Aspiration, also called suction or thrombo-suction is a method used to dislodge obstructions and/or clot by navigating a cannula, such as a catheter, through the vessels of a patients, positioning the cannula in close proximity and/or contact with the obtruction, and applying a depression or vacuum through said cannula. When successful, the depression creates a force that moves the obstruction proximally and through the cannula and can be recuperated through the proximal end of said cannula. Aspiration can be used alone or in concert with a stentriver-based mechanical thronibectomy procedure.

One of the shortcomings of the aforementioned suction method is that the catheters currently used are smaller that the target arteries they are supposed to treat. Consequently, when the aspiration begins, part of the energy of the suction goes to the aspiration of fluid promial to the distal end of the catheter. In turn, the force created by the depression on the obstruction and/or clot is greatly reduced, so is the efficiency of suction of the obstructive material and complete recanalization of the artery.

Another shortcoming of the current suction method is that it often fails to prevent the dispersion of emboli in the vasculature. These emboli can, in turn, occlude distal and/or proximal branches of the cerebrovascular tree.

Another shortcoming of current mechanical mechanical thrombectomy and thrombo-suction devices and methods is reperfusion injury. Unfortunately, abrupt restoration of blood supply to ischemic tissues may cause reperfusion injury, which is additional damage to cerebral tissue, above and beyond damage caused by the ischemia itself. For example, reperfusion results in a sudden increase in tissue oxygenation, causing a greater production of free radicals and reactive oxygen species that damage cells. The restored blood flow also brings more calcium ions to the tissues causing calcium overloading that may result in potentially fatal cardiac arrhythmias and accelerated cellular self-destruction. Furthermore, reperfusion may exaggerate the inflammation response of damaged tissue, triggering white blood cells to destroy otherwise viable damaged cells.

Reperfusion injury is highly significant and can visibly increase the infarct size (i.e., destroyed tissue) by as much as 30%. See, e.g., Andrew Tsang et al., "Myocardial Postconditioning: Reperfusion Injury Revisited," 289(1) *Am. J. Physiol. Heart & Circ. Physiol.* H2-7 (2005); Heng Zhao et al., "Interrupting Reperfusion as a Stroke Therapy: Ischemic Postconditioning Reduces Infarct Size After Focal Ischemia in Rats," 26(9) *J. Cereb. Blood Flow & Metab.* 1114-21 (2006); Giuseppe Pignataro et al., "In Vivo and In Vitro Characterization of a Novel Neuroprotective Strategy for Stroke: Ischemic Postconditioning," 28(2) *J Cereb. Blood Flow & Metab.* 232-41 (2008).

Existing thrombectomy devices and/or systems, including stent-based devices as well as thrombo-suction catheters, do not systematically or even adequately control the restoration of blood flow so as to minimize and/or prevent reperfusion injury. Thus far, the prevention of reperfusion injury has been limited to the field of interventional cardiology. During the management of an ischemic event in the heart, a cardiologist will treat the occlusion of a vessel with stents and/or balloon angioplasty to restore blood flow. Following reperfusion, a cardiologist may use an inflatable balloon to block and unblock blood flow through the vessel in intervals, thus modulating the resumed blood flow and minimizing reperfusion injury in a process called postconditioning.

Existing postconditioning devices and/or systems (e.g., catheters with high longitudinal rigidity and large diameters) are designed for the large arteries of the heart; however, the narrow and tortuous arteries of the cerebral vasculature render these existing devices and/or systems inadequate or at least less desirable in the context of ischemic stroke.

Existing postconditioning devices and/or systems also fail to incorporate simultaneous clot capture. In order to initiate reperfusion and perform postconditioning simultaneously, both a reperfusion member and flow modulation member must be disposed concurrently in the same region. Particularly in the brain, where space constraints make it difficult to fit both a reperfusion member and a flow modulation member, no existing postconditioning devices and/or systems are designed to simultaneously deploy a reperfusion member, such as a clot-capturing reperfusion member, and perform postconditioning for the ischemic tissue.

Thus, there remains a need for devices, systems, and methods designed to prevent, minimize, and/or treat ischemic stroke, and/or reduce and protect the cerebrovasculature from emboli dispersed during the treatment, and/or reperfusion injury by restoring and modulating blood flow in the cerebrovasculature.

SUMMARY OF THE INVENTION

Generally, a balloon catheter having enhanced suction capabilities for providing proximal and distal embolic protection may be used to create flow reversal within the vessel to remove clots. The additional method of post-conditioning may be incorporated with the treatment as well. Furthermore, methods of dilating the vessel, e.g., via balloon inflation, may also be optionally included to slightly dilate the vessel to help dislodge clots trapped within the vessel lumen.

The balloon suction catheter may have an outer diameter suitable for advancement through the cerebrovasculature (e.g., 3 to 8 Fr) and may incorporate a balloon and may also be fluidly coupled to a vacuum source.

In one example of use, the suction catheter may be advanced along a guidewire and positioned within the lumen of the treated vessel and into proximity of the clot. The flow in either the proximal direction or distal direction has ceased due to the presence of the clot lodged within the vessel lumen. The distal opening of the catheter may be brought into proximity (e.g., within 3 cm) of the clot or into direct contact with the clot while the balloon is located along an outer surface of the catheter near or at the distal end of the catheter and remains in a deflated low-profile configuration during advancement. With the distal opening of the catheter so positioned, a suction force may be drawn through the primary lumen of the catheter while the balloon remains in a deflated state. The primary lumen may have a diameter of between, e.g., 1 to 4 mm.

The suction force may begin to pull some portions of the clot into the primary lumen of the catheter. The blood flow through the vessel lumen may be arrested as well as through the distal regions of the vessels. With the suctioning of the clot continuing, the balloon may be inflated (e.g., via a syringe or pump fluidly coupled with the inflation lumen at the proximal end of the catheter) around the external surface of the catheter such that the balloon comes into contact with the vessel walls proximal to the clot and forms a seal to provide for proximal embolic protection as well as to inhibit any further blood flow through the region, as shown. The inflation of balloon may serve to enhance the suctioning of the clot into the primary lumen of the catheter by preventing blood from flowing distally past the catheter and clot and creating a localized region of low pressure between the expanded balloon and clot.

The inflated balloon may also prevent blood flow from carrying debris from the clot further downstream into the narrower cerebral arteries to prevent any distal embolization. Additionally, the inflation of balloon also controls the onset of reentry of blood flow reperfusion.

As the clot is further evacuated, the seal created by the balloon against the vessel wall may be maintained and the suction continued within the primary lumen as the flow begins to increase until a retrograde effect is produced and flow reversal of the blood is created in the treated vessel and distal vessels. The guidewire may be may be removed from the vessel lumen prior to, during, or after balloon inflation. The flow reversal provides distal embolic protection by drawing any emboli from the clot proximally through the vessels and into the primary lumen. The blood flow may be monitored using, e.g., contrast dye and angiography or other imaging modalities to ascertain whether some measure of blood flow through the vessel has been restored.

If blood flow has not been adequately restored, or enough of the clot has not been adequately removed, the operator may choose to use any number of mechanical intervention such as a clot-pulling device. The clot-pulling device may generally comprise a microcatheter having an outer diameter of e.g., 1 to 4 Fr, or some other mechanical device which may be disposed though the primary lumen and directly engages with the clot, e.g., with a clot retrieval device.

The operator may perform cycles of blocking and unblocking the cerebral artery using the balloon post-recanalisation. This procedure is known as post-conditioning and reduces reperfusion injury, the damage to brain tissue dealt by the sudden reentry of blood flow and the oxygen carried by the blood into ischemic tissue. The cycles of blocking and unblocking flow are created by inflation and deflation of the balloon. The movement of balloon inflating fluid into the balloon causes inflation and the movement of balloon inflating fluid out of the balloon causes deflation. Drugs may be introduced (e.g., intravenously, through the primary lumen, through a separate drug delivery lumen, etc.) to aid in clot removal, clot dissolution, treating reperfusion injury or otherwise aiding recovery.

A further treatment option may include post-conditioning using the same treatment catheter where the post-conditioning procedure may be initiated after the clot and any debris has been evacuated through the primary lumen of the catheter. The balloon may be deflated to allow for the downstream flow of blood past the balloon and into the distal vessel lumens. The balloon may then be re-inflated to again arrest the flow of blood and then deflated once again to allow blood flow in the distal direction. This deflation and re-inflation may be performed a number of times, e.g., at least twice, to modulate the amount of oxygenated blood reaching the ischemic tissue to post-condition the vessel. Once the post-conditioning has been completed, the balloon may be deflated and the catheter removed from the body.

An additional method which may be optionally utilized with the catheter for removal of the clot from within the vessel may include overinflating the balloon by introducing additional fluid into the balloon interior such that the diameter of the balloon is increased by, e.g., 4% to 50%, such that the diameter increases by, e.g., 2.5 to 3.75 mm. The overinflated balloon may push the contacted vessel walls radially outward such that the clot may dislodge, at least partially, from the vessel walls. The balloon may be overinflated and left in its expanded configuration during clot suctioning; alternatively, the balloon may be overinflated, deflated back to its initial inflation state, and overinflated again to facilitate dislodgement of the clot from the vessel wall. This process may be repeated as few or as many times as needed or desired to facilitate dislodgement.

Turning now to the catheter itself, the wall of the secondary balloon inflation lumen may be formed or otherwise attached to the external wall of the primary lumen such that the secondary lumen is formed externally of the primary lumen. The inflation balloon may accordingly be formed at least partially upon the external wall of the primary lumen and over the external wall of the secondary lumen such that the secondary lumen terminates within the interior of the balloon. The secondary lumen may be fluidly coupled to the interior of the balloon, for instance, through one or more infusion openings, which provide a fluid path for the inflation fluid to be evenly distributed within the balloon interior. Alternatively, the secondary lumen may terminate in a single opening within the balloon interior.

Turning now to the secondary inflation lumen, one variation may include where the secondary lumen may be shaped in an arcuate configuration and formed within the wall of the primary lumen. Another variation may include where the secondary lumen may also be formed within the wall of the primary lumen but having a relatively narrower configuration. Another variation may include where the secondary lumen is formed partially upon the wall of the primary lumen surrounded by the external wall of the secondary lumen such that the secondary lumen has a curved rectilinear configuration. Yet another variation may have the secondary lumen formed as a separate arcuate lumen external to the wall.

With respect to some of the various layout configurations into which the secondary lumen may be formed upon the external surface of the wall of the primary lumen, one variation may include where the secondary lumen is simply formed in a straightened configuration, which follows in parallel the longitudinal axis of the primary lumen. Another variation may include where multiple secondary lumens may be aligned in parallel for fluid connection to the balloon. Yet another variation may include where the secondary lumen may be configured to follow along the wall of the primary lumen in a helical configuration. This configuration, as well as the other configurations, may be incorporated to facilitate the bending and tortuous shapes that the catheter may undergo during use. Yet another variation may include where the secondary lumen may be configured to follow a path around the catheter external wall but where the secondary lumen forms parallel and transverse configurations relative to the longitudinal axis of the catheter.

Some various configurations where the catheter may be configured to provide for structural robustness while maintaining adequate flexibility for advancement within the cerebrovasculature may include where the wall of the primary lumen may be formed to have an inner liner with a reinforcement member which is configured as a coiled member wound helically around the inner liner. An external jacket may be formed externally around both the reinforcement member and inner liner. The external jacket may also form the externally positioned secondary lumen.

BRIEF DESCRIPTION OF THE DRAWINGS

FIGS. 4A to 4H illustrate another variation for removing a clot via a treatment catheter with suctioning followed by post-conditioning.

FIGS. 7A and 7B illustrate detail cross-sectional side views of different variations of a secondary inflation lumen located externally of the primary lumen.

FIGS. 8A to 8F illustrate cross-sectional end views of different configurations for the secondary inflation lumen relative to the primary lumen.

DETAILED DESCRIPTION OF THE INVENTION

Apparatus and methods of treating patients suffering from cardiovascular maladies encompassing embolisms and thromboembolisms may be used to create a temporary vascular occlusion in combination with suction of emboli. Particularly, instruments and methods for enhanced suction of emboli, the combined activity of inflating balloons in the diseased vessels, once or multiple times, concomitantly or sequentially with applying vacuum to dislodge and remove thrombus or emboli in the vasculature may be used.

Generally, a balloon catheter having enhanced suction capabilities for providing proximal and distal embolic protection may be used to create flow reversal within the vessel to remove clots. The additional method of post-conditioning may be incorporated with the treatment as well. Furthermore, methods of dilating the vessel, e.g., via balloon inflation, may also be optionally included to slightly dilate the vessel to help dislodge clots trapped within the vessel lumen.

Figure 1:
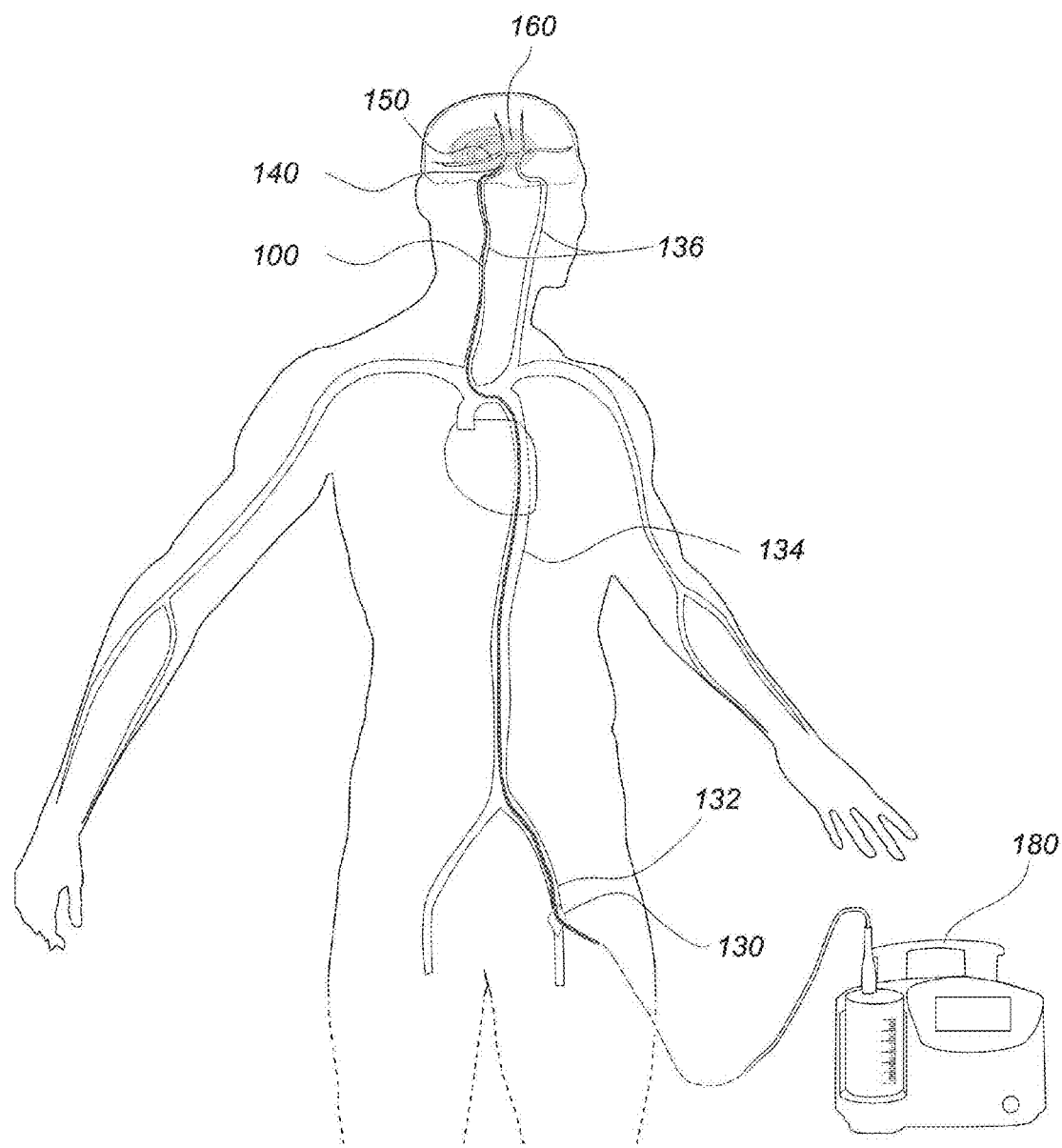
FIG. 1 illustrates one example of accessing the cerebrovasculature by accessing the vasculature via a femoral artery to treat a clot.

In treating a patient who has undergone a stroke, a neurosurgeon or interventional neuroradiologist may guide a balloon suction catheter 100 from, e.g., an incision 130 in the femoral artery 132 and through the blood vessels of the heart (such as the aorta 134) and neck (such as the carotid artery 136) and to a position in proximity of the infarcted region of the brain 160 adjacent to the clot 150, e.g., within 3 cm of the clot 150. The balloon suction catheter 100, as described in detail herein, may have an outer diameter suitable for advancement through the cerebrovasculature (e.g., 3 to 8 Fr) and may incorporate a balloon 140 and may also be fluidly coupled to a vacuum source 180, as illustrated in the example of FIG. 1.

Figure 2:
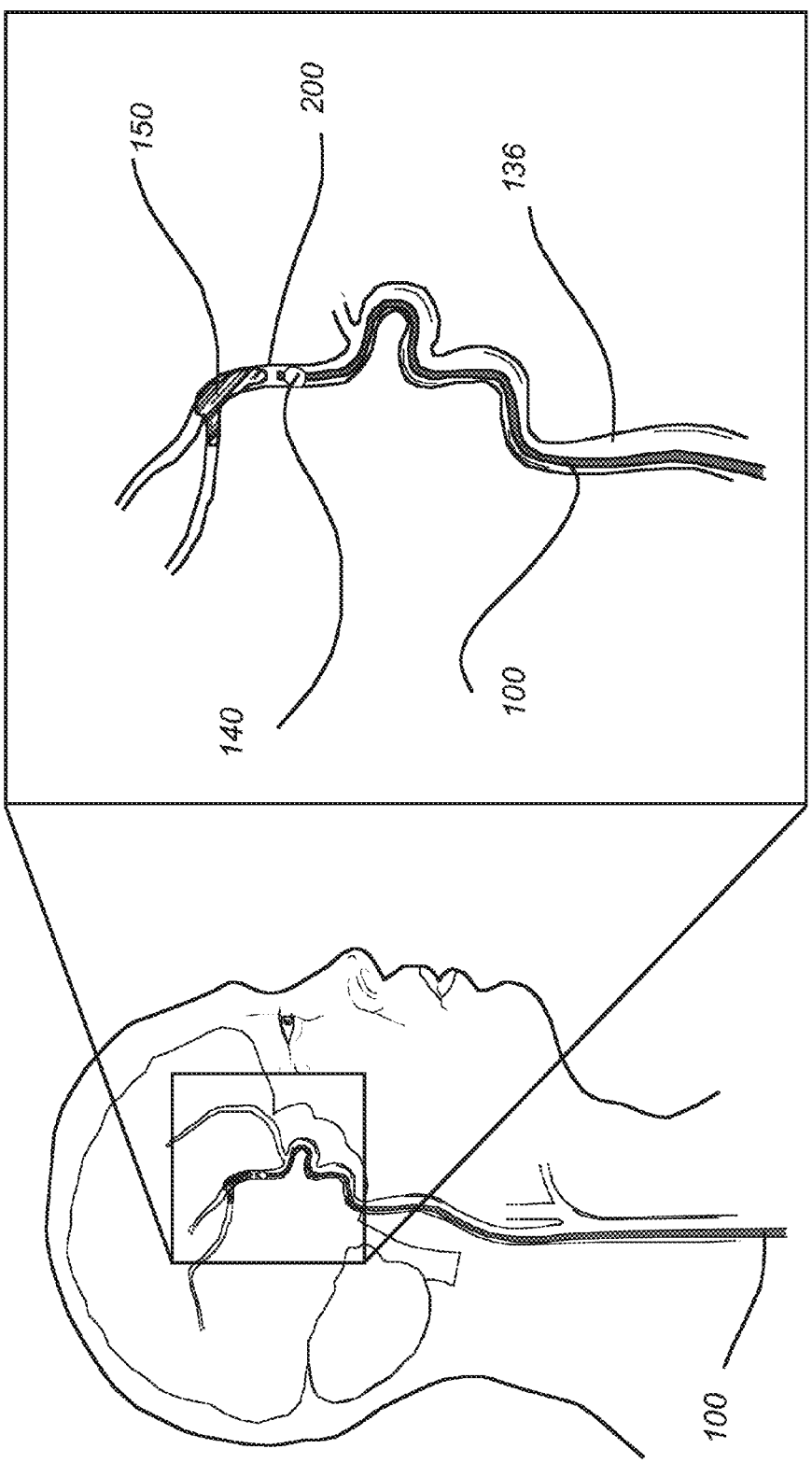
FIG. 2 illustrates a detail example of the tortuous nature of the cerebrovasculature in approaching a clot using a treatment catheter and methods as described.

FIG. 2 shows a detail illustration of how the suction catheter 100 may be advanced through, e.g., the carotid artery 136 such that the balloon 140 and distal end of the catheter 100 is positioned into proximity of the clot 150. In this example, the clot 150 is illustrated as being lodged within and accessed through, e.g., the middle cerebral artery 200, although the catheter and methods of its use are not so limited to use in particular vasculature.

Figure 3A:
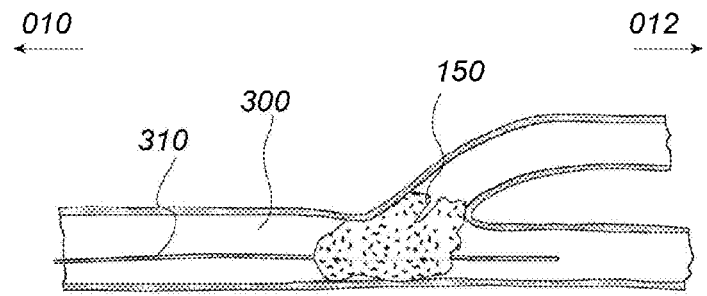
FIGS. 3A to 3E illustrate one variation for removing a clot via a treatment catheter which can induce flow reversal to enhance distal protection during clot removal.
Figure 3B:
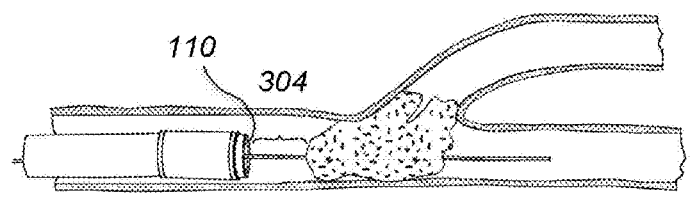
Figure 3C:
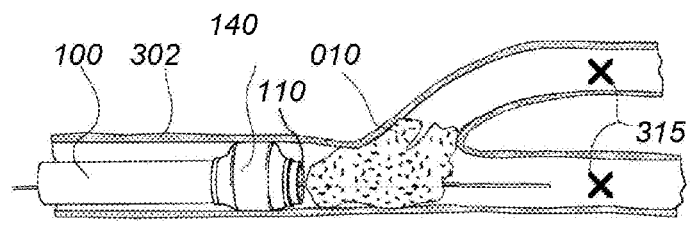

In one example of use, FIGS. 3A to 3E illustrate how the suction catheter 100 may be advanced along a guidewire 310 and positioned within the lumen 300 of the treated vessel and into proximity of the clot 150. As shown in FIG. 3A, the flow in either the proximal direction 010 or distal direction 012 has ceased due to the presence of the clot 150 lodged within the vessel lumen 300. The distal opening of the catheter 100 may be brought into proximity 304 (e.g., within 3 cm) of the clot 150, as shown in FIG. 3B, or into direct contact with the clot 150 while the balloon 140 is located along an outer surface of the catheter 100 near or at the distal end of the catheter 100 and remains in a deflated low-profile configuration during advancement. With the distal opening of the catheter 100 so positioned, a suction force may be drawn through the primary lumen 110 of the catheter 100 while the balloon 140 remains in a deflated state. The primary lumen 110 may have a diameter of between, e.g., 1 to 4 mm.

The suction force may begin to pull some portions of the clot 150 into the primary lumen 110 of the catheter 100. The blood flow through the vessel lumen 300 may be arrested as well as through the distal regions of the vessels, as indicated by flow arrest 315, shown in FIG. 3C. With the suctioning of the clot 150 continuing, the balloon 140 may be inflated (e.g., via a syringe or pump fluidly coupled with the inflation lumen at the proximal end of the catheter 100) around the external surface of the catheter 100 such that the balloon 140 comes into contact with the vessel walls proximal to the clot 150 and forms a seal to provide for proximal embolic protection as well as to inhibit any further blood flow through the region, as shown. The inflation of balloon 140 may serve to enhance the suctioning of the clot 150 into the primary lumen 110 of the catheter 100 by preventing blood from flowing distally past the catheter 100 and clot 150 and creating a localized region of low pressure between the expanded balloon 140 and clot 150. The balloon 140 may have a length of between, e.g., 2 and 12 mm, and a diameter of between, e.g., 1.2 to 4.2 mm, in the deflated state and between, e.g., 1.5 to 5 mm, in the inflated state.

Figure 3D:
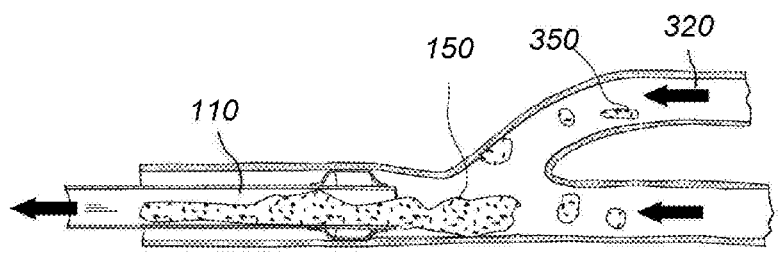
Figure 3E:
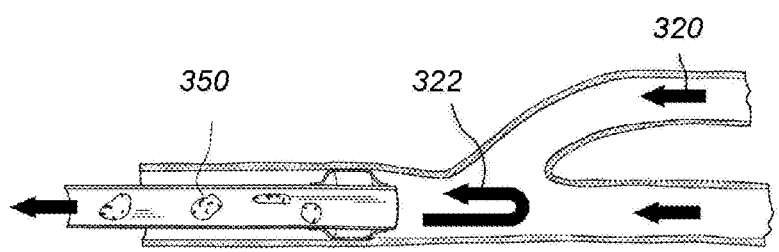
Figure 3F:
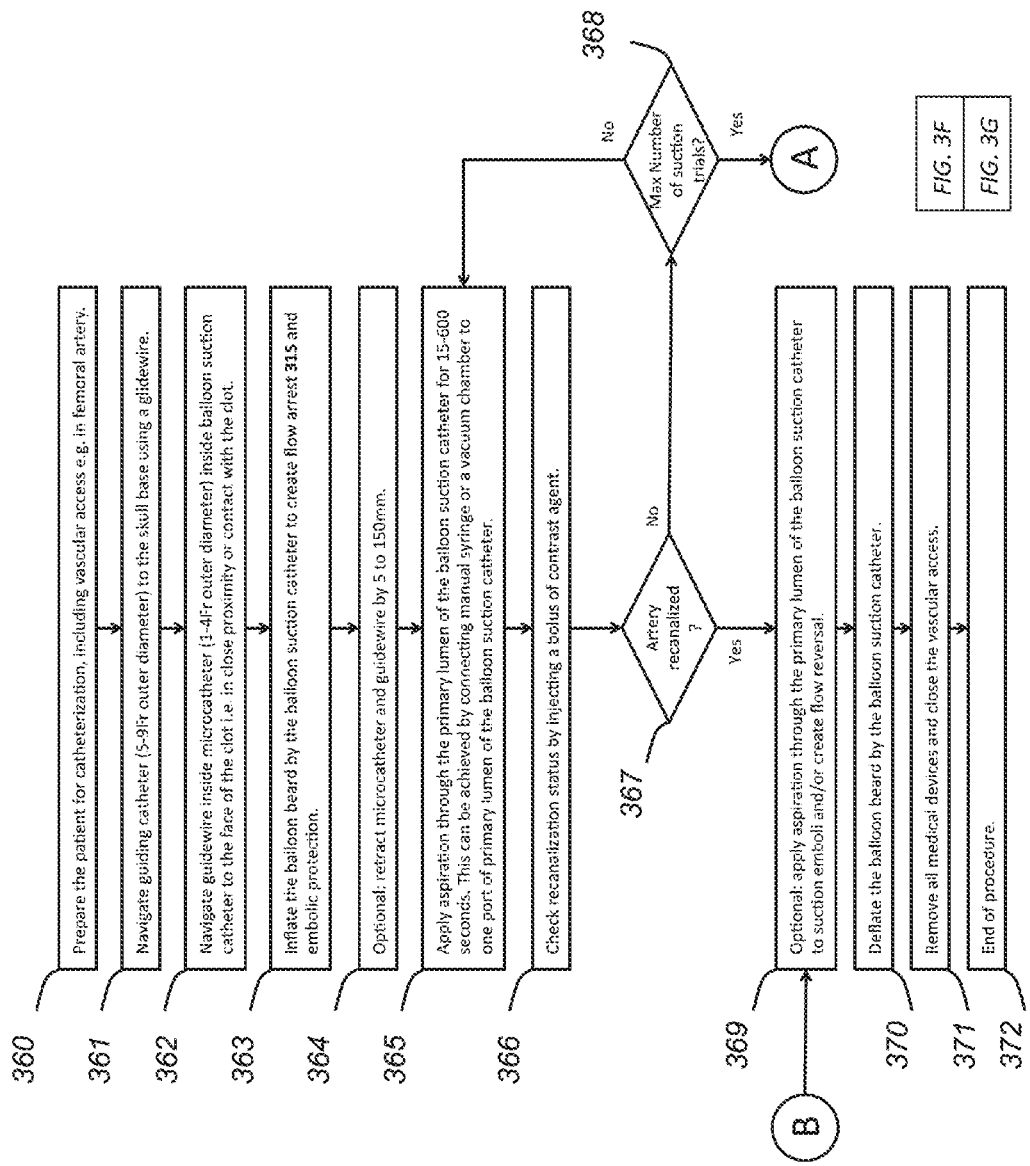
FIGS. 3F and 3G illustrate flow diagrams which describe examples of a suction procedure used with a balloon to enhance the suctioning and embolic protection.
Figure 3G:
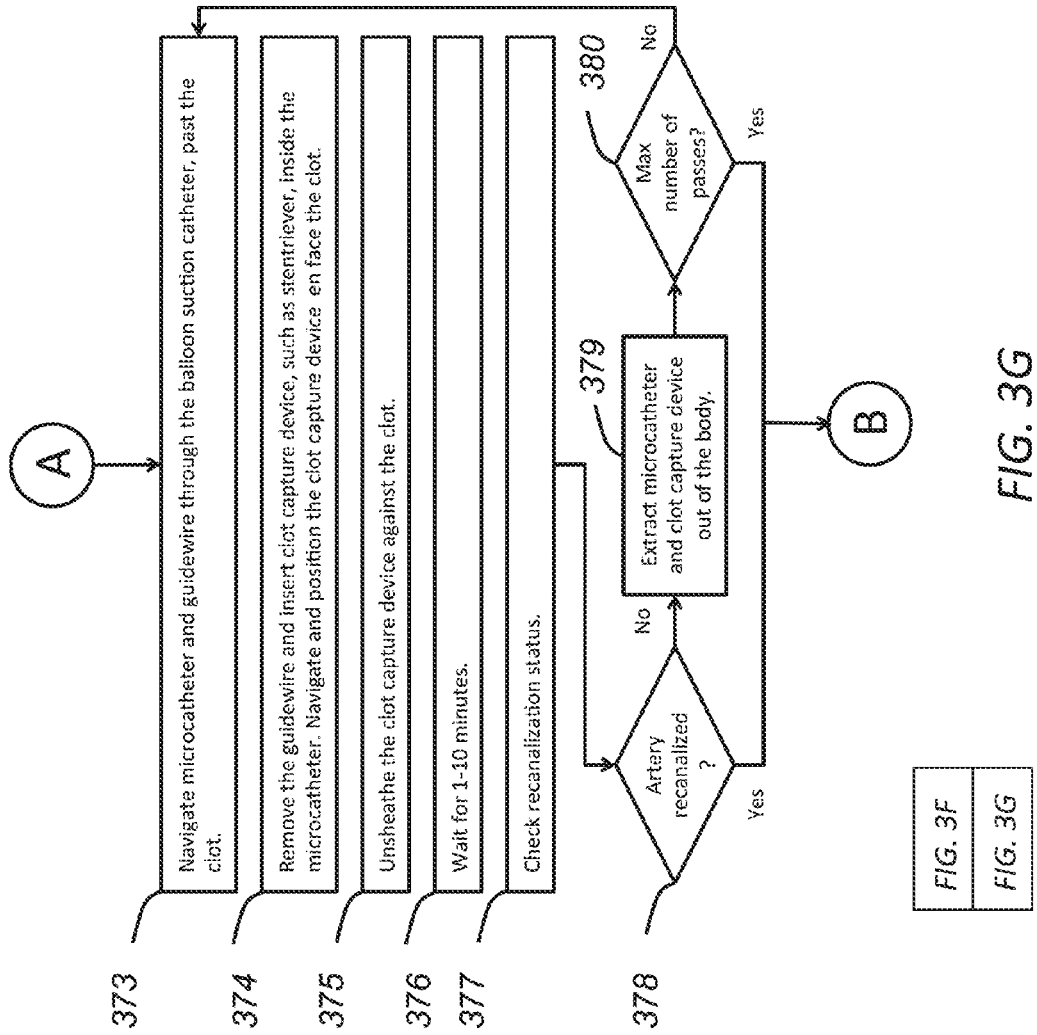
Figure 3H:
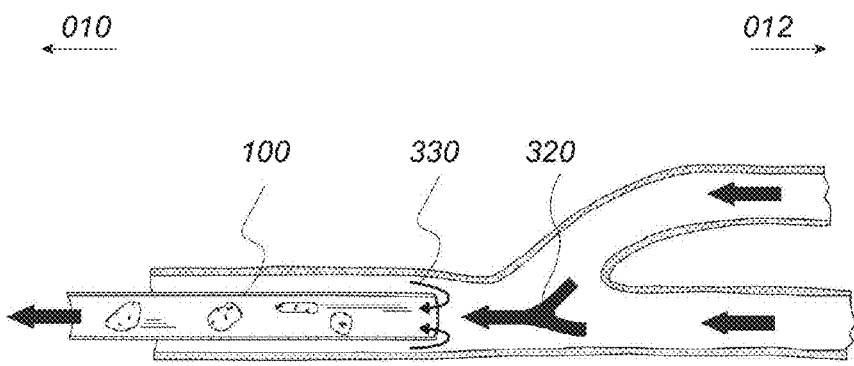
FIGS. 3H to 3J illustrate an example of how the balloon may facilitate an aspiration procedure with in the vessel.
Figure 3I:
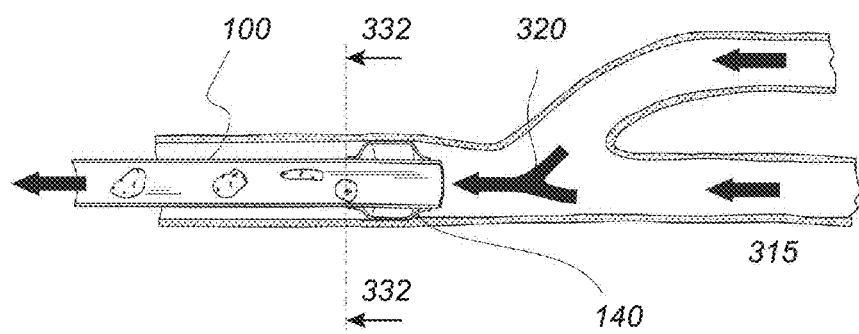
Figure 3J:
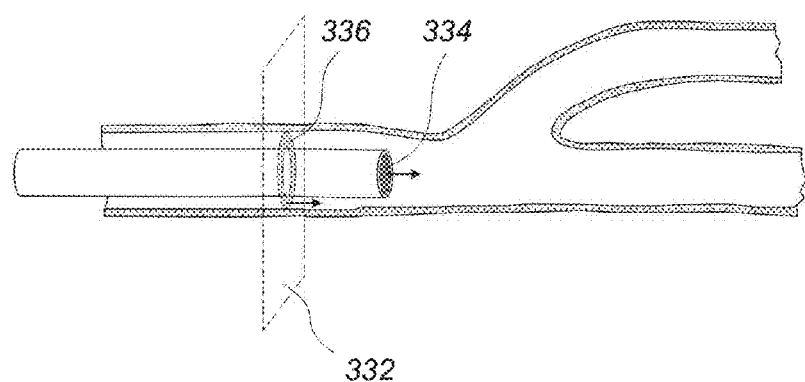
Figure 3K:
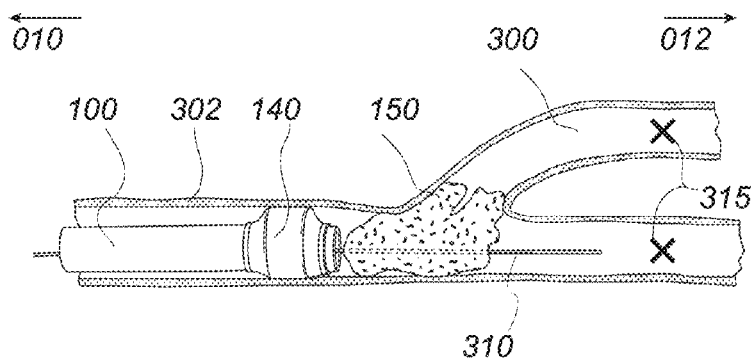
FIGS. 3K to 3O illustrate a variation where a microcatheter may be introduced through the primary lumen to provide a mechanical intervention to treat the clot.

In another example of use, FIGS. 3H to 3J illustrate how the inflation of the balloon may enhance suction by eliminating the flow 330 of blood coming proximally to the distal end of catheter 100 and being aspirated in the primary lumen 110. As shown in FIG. 3J, the inflation of the balloon 140 may increase the suctioning efficiency where the efficiency, E, may be determined by the following:

$$E = \frac{|Q_{catheter}| - |Q_{proximal}|}{|Q_{catheter}|} \quad (1)$$

$$Q_{catheter} = \iint_{A_1} v \cdot dA \quad (2)$$

$$Q_{proximal} = \iint_{A_2} v \cdot dA \quad (3)$$

where, $Q_{catheter}$=the flow rate through the surface $A_1$ 334, orthogonal to the centerline of primary lumen 110 at its distal end, during suction $Q_{proximal}$=the flow rate through the surface $A_2$ 336, defined by the annulus between the suction catheter 100 and the vessel wall 302 in the plane 332, orthogonal to the centerline of the primary lumen 110 at the proximal end of the balloon 140, during suction v=the velocity of the fluid The inflated balloon 140 may also prevent blood flow from carrying debris from the clot 150 further downstream into the narrower cerebral arteries to prevent any distal embolization. Additionally, the inflation of balloon 140 also controls the onset of reentry of blood flow reperfusion.

As the clot 150 is further evacuated, the seal created by the balloon 140 against the vessel wall may be maintained and the suction continued within the primary lumen 110 as the flow begins to increase until a retrograde effect 322 is produced and flow reversal 320 of the blood is created in the treated vessel and distal vessels, as shown in FIG. 3D. The guidewire may be 310 and optionally microcatheter 312 may be used to advance the balloon suction catheter 100 to the face of the clot or they may be removed from the vessel lumen prior to, during, or after balloon inflation. The flow reversal provides distal embolic protection by drawing any emboli 350 from the clot 150 proximally through the vessels and into the primary lumen 110, as shown in FIG. 3E. The blood flow may be monitored using, e.g., contrast dye and angiography or other imaging modalities to ascertain whether some measure of blood flow through the vessel has been restored.

Figure 3L:
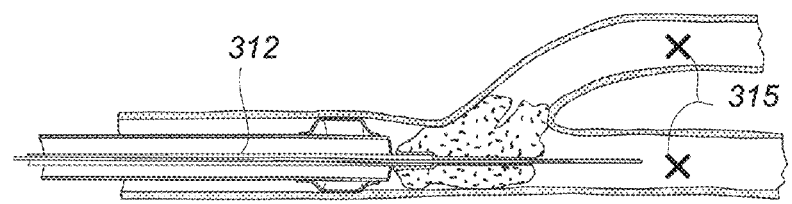
Figure 3M:
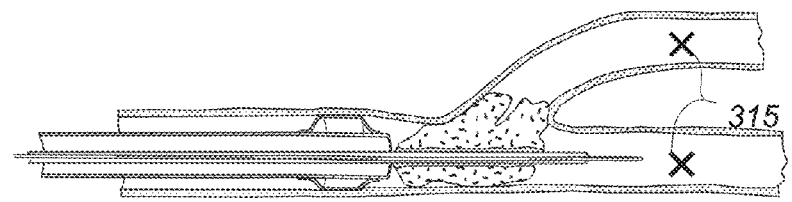
Figure 3N:
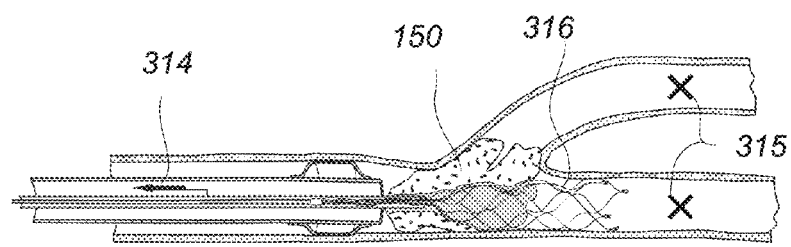
Figure 3O:
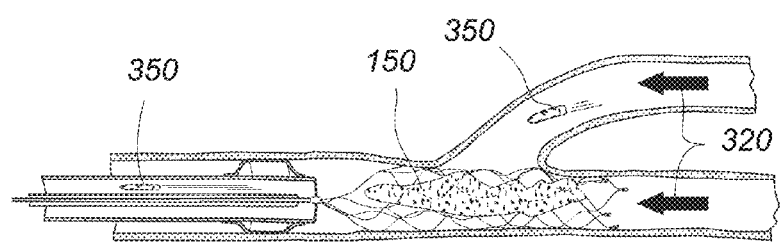

If blood flow has not been adequately restored, or enough of the clot 150 has not been adequately removed, the operator may choose to use any number of mechanical intervention such as a clot-pulling device, as shown in FIGS. 3K to 3O. In particular, FIGS. 3L and 3M show how the microcatheter 312 advances through the clot 150, a technique sometimes referred to as "Dottering", which can generate emboli 350. FIG. 3N illustrates how the guidewire 310 is pulled out from the microcatheter 312 and substituted for a clot-pulling device 316, such as a stentriever, placed vis-à-vis the clot, and pulling 314 of the microcatheter 312 unsheathes the clot-pulling member that may re-establish part or all of the cross-sectional area available for blood. Pulling the clot-capture device 316 and the microcatheter 312, and dragging the clot 150 inside catheter 100 may yet again create emboli. In one example of use, the inflation of balloon 140 may achieve flow arrest 315, prevent emboli 350 from escaping with the flow in the distal cerebrovasculature and aspirating these emboli as seen in FIG. 3O.

The clot-pulling device may generally comprise a microcatheter 312 having an outer diameter of, e.g., 1 to 4 Fr, or some other mechanical device which may be disposed though the primary lumen 110 and directly engages with the clot 150, e.g., with a clot retrieval device 316.

The operator may perform cycles of blocking and unblocking the cerebral artery using the balloon so as to modulate the blood flow through the treated vessel. This procedure is known as post-conditioning and reduces the damage to brain tissue known as reperfusion injury, which is caused by the sudden reentry of blood flow and the oxygen carried by the blood to ischemic tissue. The cycles of blocking and unblocking the vessel, e.g. decreasing and increasing flow, are created by inflation and deflation of the balloon. The movement of balloon inflating fluid into the balloon causes inflation and the movement of balloon inflating fluid out of the balloon causes deflation. Drugs may be introduced (e.g., intravenously, through primary lumen 110, through a separate drug delivery lumen, etc.) to aid in clot removal, clot dissolution, treating reperfusion injury or otherwise aiding recovery.

FIGS. 3F and 3G show a flow diagram illustrating details of the method for treating a clot within a vessel by providing suction, embolic protection, and flow reversal within the vessel. In particular, in step 360 the patient may initially be prepared for catheterization, including obtaining vascular access, e.g., in a femoral artery. The catheter may be guided to the base of the skull using a guidewire in step 361. The guidewire may be navigated inside the catheter such that the suction catheter is brought into close proximity or contact with the clot in step 362. The balloon on the catheter may be inflated to create flow arrest and to provide proximal embolic protection in step 363. The catheter and guidewire may be optionally retracted by, e.g., 5 to 150 mm, in step 364. Aspiration may then be applied through the primary lumen of the catheter for, e.g., 15 to 600 seconds (although this time may be varied) in step 365 and recanalization status may be checked in step 366, e.g., by injecting a bolus of a contrast agent or through another modality.

If the artery has not been recanalized per step 367, a check may be done to determine if a maximum number of suction trials has been done per step 368. If not, then the aspiration may be continued but if the maximum number has been reached, then a microcatheter and guidewire may be navigated through the primary lumen of the catheter and past the clot per step 373 and the clot may be removed by mechanically using, e.g., a stent retriever deployed from the catheter by unsheathing a clot capture member against the clot per steps 374, 375. After a period of time, e.g., 1 to 10 minutes, per step 376, the recanalization status may be checked again per step 377 to determine if the artery is recanalized per step 378. If the artery has not recanalized, the mechanical intervention may be repeated to capture the clot 379 while determining if a maximum number of passes have been performed 380. If not, the mechanical intervention may be repeated 380 but if so, aspiration may be optionally applied through the primary lumen of the balloon catheter to suction emboli and/or create flow reversal per step 369. The balloon may be deflated per step 370 and instrument removed 371 to end the procedure per step 372.

FIGS. 4A to 4E illustrate the treatment and removal of a clot 150 from within the vessel lumen 300 as described above in FIGS. 3A to 3E but further includes the additional treatment option of post-conditioning using the same treatment catheter 100. FIGS. 4F to 4H illustrate one variation where the post-conditioning procedure may be initiated after the clot 150 and any debris 350 has been evacuated through the primary lumen 110 of the catheter 100. As illustrated in FIG. 4F, the balloon 140 may be deflated to allow for the downstream flow 420 of blood past the balloon 140 and into the distal vessel lumens 422. The balloon 140 may then be re-inflated to again arrest the flow 315 of blood, as shown in FIG. 4G, and then deflated once again to allow for the distal blood flow 420, as shown in FIG. 4H. This deflation and re-inflation may be performed a number of times, e.g., at least twice, to modulate the amount of oxygenated blood reaching the ischemic tissue to post-condition the vessel. Once the post-conditioning has been completed, the balloon 140 may be deflated and the catheter 100 removed from the body.

The postconditioning procedure may be performed manually by the operator, using a syringe to inflate and deflate the balloon, and an instrument for measuring time, e.g. a chronometer, to implement the postconditioning scheme. Alternatively, the postconditioning procedure may be performed automatically by connecting a programmable pump or controller fluidly coupled to the secondary lumen 720 of the balloon suction catheter 100.

Figure 4A:
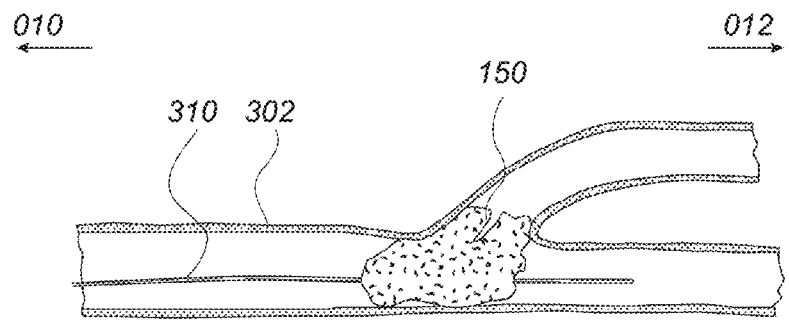
Figure 4B:
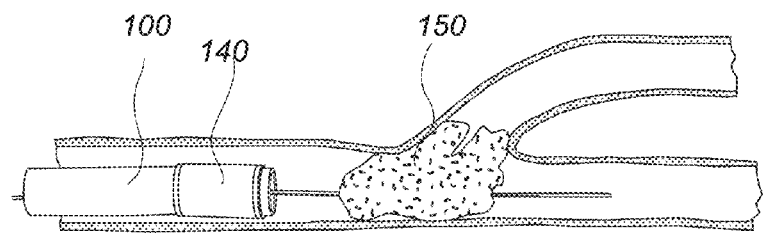
Figure 4C:
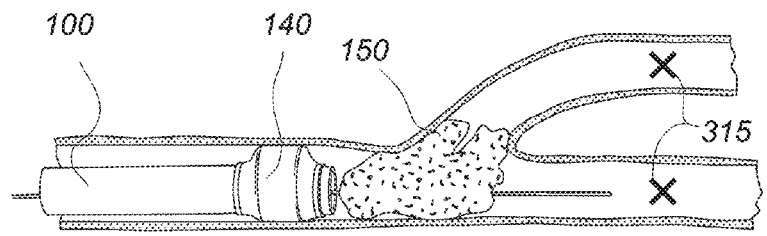
Figure 4D:
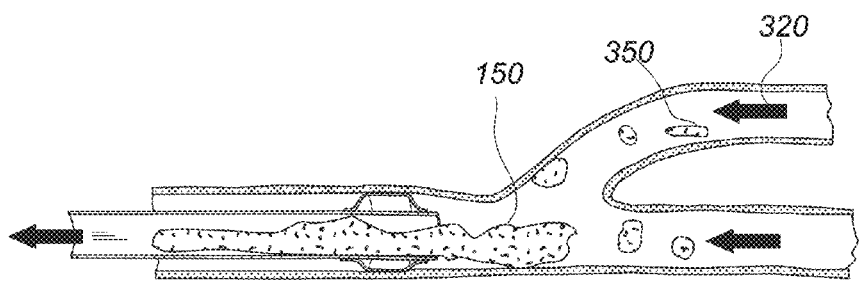
Figure 4I:
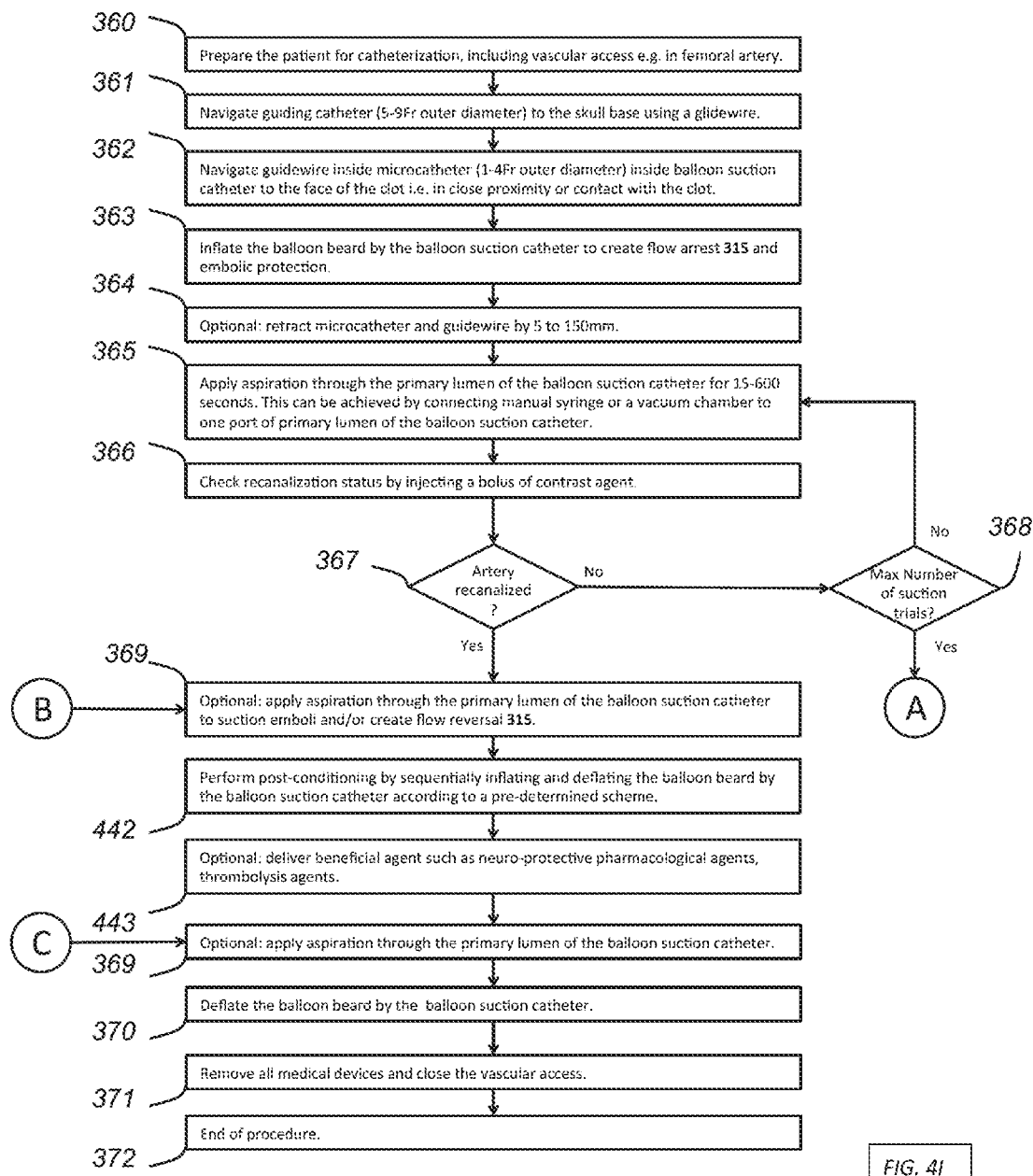
FIGS. 4I and 4J illustrate flow diagrams for a suction procedure followed by post-conditioning.
Figure 4J:
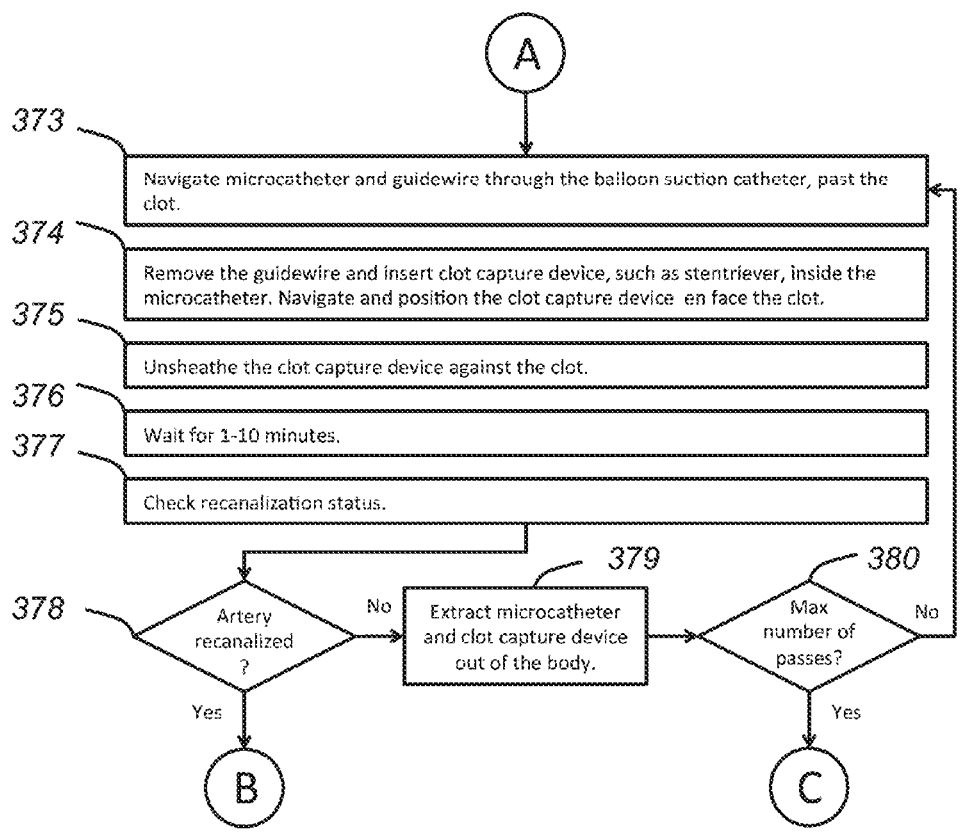

FIGS. 4I and 4J show a flow diagram illustrating details of the method for treating a clot within a vessel by providing suction, embolic protection, and flow reversal within the vessel similar to that shown in FIGS. 3F and 3G but with the addition of post-conditioning. After aspiration has been applied through the primary lumen to suction emboli and/or to create flow reversal per step 369 (as described above), post-conditioning may be performed by sequentially inflating and deflating the balloon according to a pre-determined process, as described herein, per step 442.

Optionally, a beneficial agent such as a neuro-protective pharmacological agent, thrombolysis agent, etc. may be administered per step 443. Additionally, in the event that a mechanical intervention was performed for removing the clot, if it is determined that a maximum number of passes was achieved per step 380, the aspiration may be then optionally applied directly through the primary lumen of the balloon catheter per step 369 and the post-conditioning steps may be by-passed.

The number and length of the time intervals for post-conditioning methods of reperfusion may be accomplished in a number of different ways, as shown in the various examples of post-conditioning cycles in FIGS. 4K to 4O. Further details may be seen in WO 2014/008460 (PCT/US2013/049428 filed Jul. 5, 2013 and designating the U.S.) as well as U.S. Pub. 2014/0155980 (U.S. patent application Ser. No. 13/844,728 filed Mar. 15, 2013) and U.S. Pub. 2015/0230820 (U.S. patent application Ser. No. 14/412,387 filed Jul. 5, 2014), each of which is incorporated herein by reference in its entirety and for any purpose herein.

In each of FIGS. 4K to 4O, the y-axis represents the percentage of the cross-sectional luminal area of the blood vessel spanned by the flow modulation member normalized to its constrained state. Therefore, these graphs do not take into account the effect of the clot or changes in unblocked space around the clot (i.e., if the flow modulation member is expanded so that it is stretches across 75% of the blood vessel, then the graph at that point in time is 75% shaded.) The x-axis is time in seconds. For example, the operator may choose more and/or longer cycle periods when the time from the onset of the ischemia is greater.

Figure 4K:
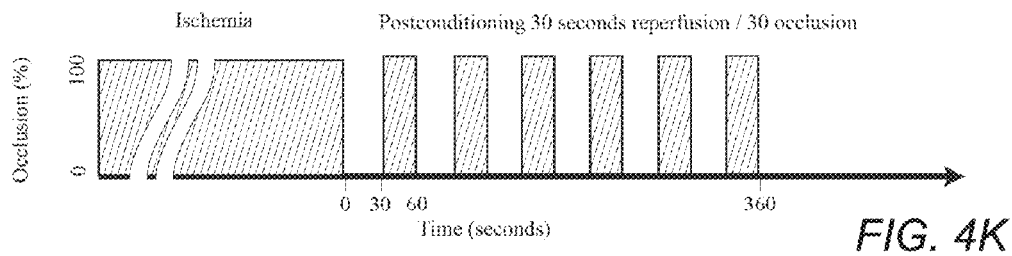
FIGS. 4K to 4O illustrate various post-conditioning methods which may be utilized with the treatment catheter.

FIG. 4K illustrates one variation where the interval schedule may be about 6 alternating intervals of approximately 30 seconds unblocked and 30 seconds blocked. The number of cycles (flow/no flow) may vary and may be between, e.g., 2 and 20.

Figure 4L:
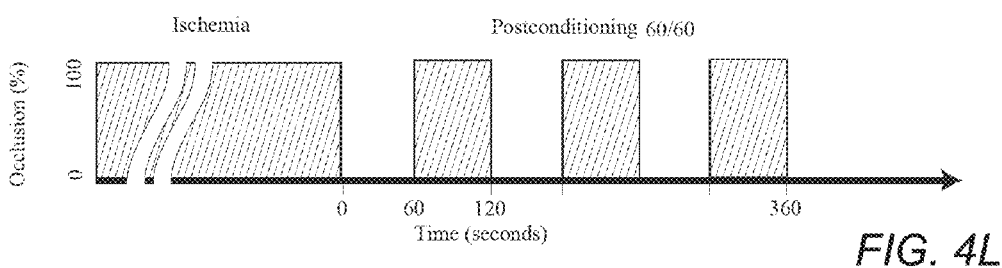

FIG. 4L illustrates another variation of an interval schedule with 3 alternating intervals of approximately 60 seconds unblocked and 60 seconds blocked. The transitions from unblocking to blocking as well as the transitions from blocking to unblocking occur rapidly as is indicated by the vertical slope on either side of the shaded (blocking) areas.

Figure 4M:
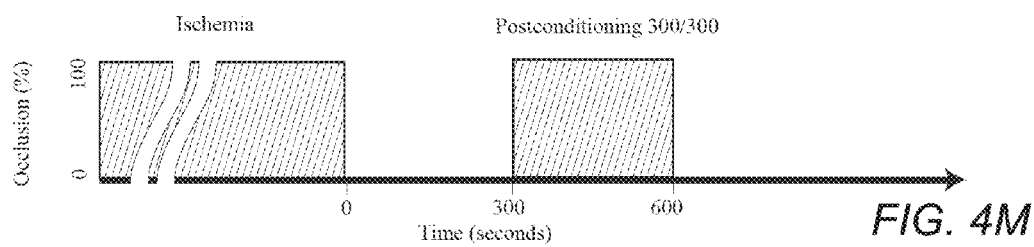

FIG. 4M illustrates another variation of an interval schedule with 1 alternating interval of approximately 300 seconds (five minutes) unblocked and 300 seconds blocked. The transitions from unblocking to blocking as well as the transitions from blocking to unblocking occur rapidly as is indicated by the vertical slope on either side of the shaded (blocking) area.

Figure 4N:
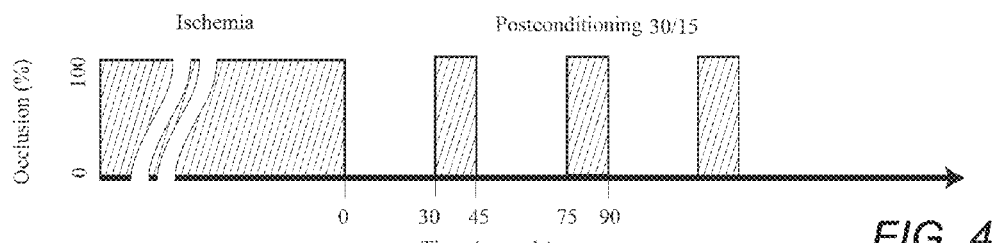

FIG. 4N illustrates another variation where the unblocked time is not equal to the blocked time, within the cycles. The different parts of the cycle can be of disparate time spans and may vary across cycles as well. This particular variation includes an interval schedule with 3 alternating intervals of approximately 30 seconds unblocked and 15 seconds blocked. The transitions from unblocking to blocking as well as the transitions from blocking to unblocking occur rapidly as is indicated by the vertical slope on either side of the shaded (blocking) areas.

Figure 4O:
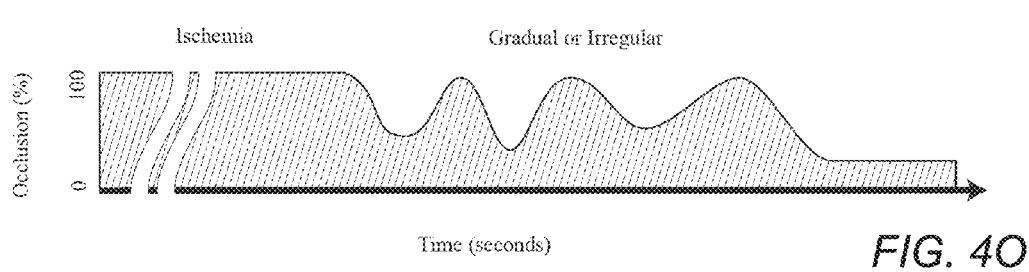

FIG. 4O illustrates another variation a gradual or partial occlusion with a flow modulation member where the degree of occlusion is non-linear. Meanwhile, the flow modulation member is deployed gradually for slower and steadier occlusion of a blood vessel. Post-conditioning is performed as close to the onset of reperfusion as possible. The actual degree of reperfusion achieved, as compared to normal flow rates, may vary depending on the degree to which reperfusion is achieved by the reperfusion member or the degree to which occlusion is achieved by the flow modulation member.

Each of the Embodiments of the flow modulation system or devices may also be used with chemicals, pharmaceuticals, or other agents to, for example: further minimize reperfusion injury, aid in removing a clot, or otherwise benefit a patient's condition. Agents that may minimize reperfusion injury include cyclosporine, sodium-calcium Na2+/Ca2+ exchange inhibitors, monoclonal antibodies, temperature reducing agents, or agents that slow cell metabolism. Agents that may aid in removing a clot include tPA and other agents that aid in dissolving, dislodging, or macerating clots. Agents that may otherwise benefit the patient's condition include pharmaceuticals commonly used for treating clots; agents for treating clots, preventing restenosis, or that commonly coat intravascular devices such as vasodilators; nimodipine; sirolimus; paclitaxel; anti-platelet compounds; agents that promote the entanglement or attachment of a clot with a reperfusion member; and anticoagulants such as heparin.

Figure 5A:
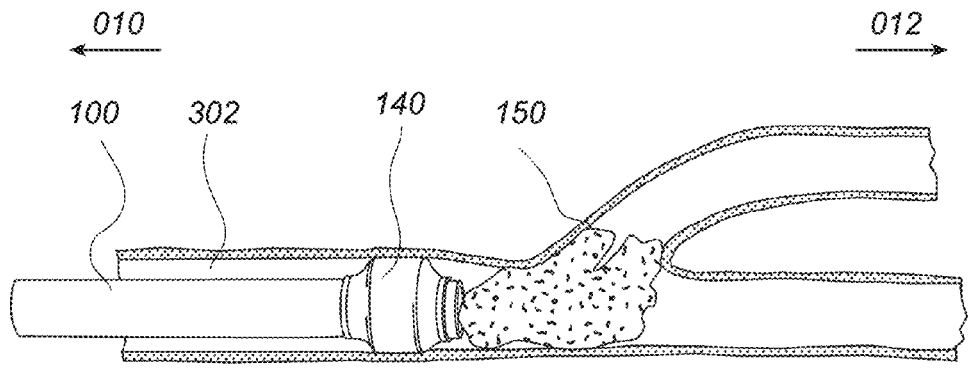
FIGS. 5A and 5B illustrate another variation for facilitating the dislodgement of the clot from the vessel walls by over-inflation of the balloon along the catheter.
Figure 5B:
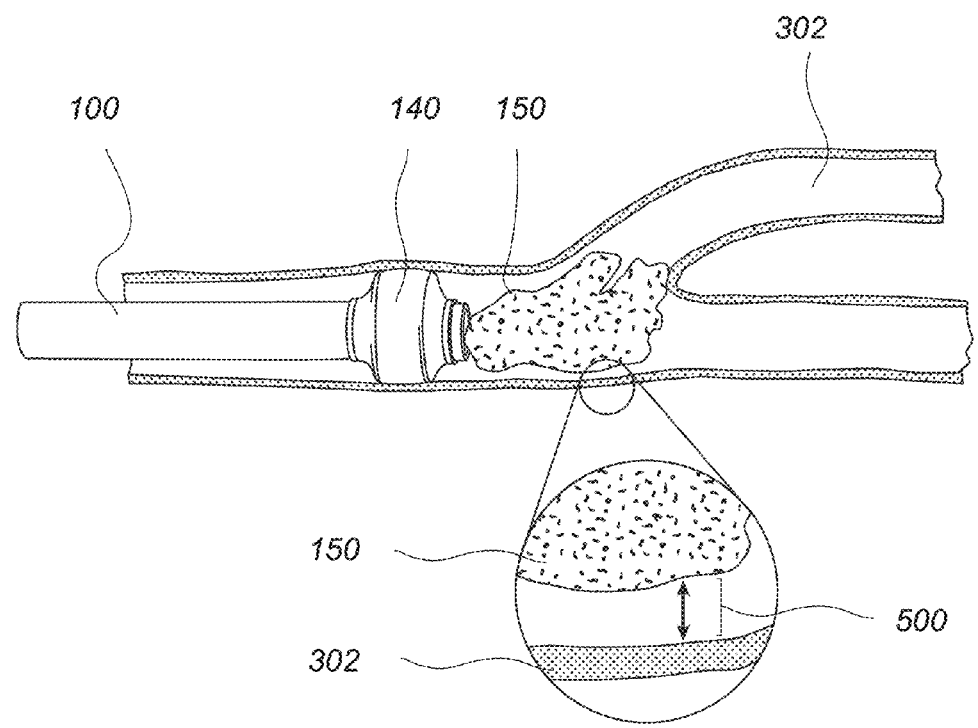

FIGS. 5A and 5B illustrate an additional method, which may be optionally utilized with the catheter 100 for removal of the clot 150 from within the vessel. For example, as shown in FIG. 5A, as the clot 150 is suctioned into the primary lumen 110 and the balloon 140 is inflated into contact against the vessel interior wall, the balloon 140 may be overinflated by introducing additional fluid into the balloon interior such that the diameter of the vessel is increased by, e.g., 4% to 50% compared to its normal diameter during diastole, when no medical instrument is inserted, such that the diameter increases by, e.g., 2.5 to 3.75 mm. We define the expression "normally inflated" for balloon 140 as a state in which the outer surface of its membrane contacts the vessel wall 302 without significantly dilating the vessel, e.g. less that 4% of its normal diameter, and decreases flow past the balloon 140 to a negligible quantity, also referred as occlusion. The expression "overinflated" defines a state in which the membrane of balloon 140 exerts an outwardly radial force on the vessel that increases its inner diameter by at least 4% compared to its normal state. The overinflated balloon 140 may push the contacted vessel walls radially outward such that the clot 150 may dislodge, at least partially, from the vessel walls 302 as indicated by gap 500 shown in FIG. 5B. The balloon 140 may be overinflated and left in its expanded configuration during clot suctioning; alternatively, the balloon 140 may be overinflated, deflated back to its initial inflation state, and overinflated again to facilitate dislodgement of the clot 150 from the vessel wall 302. This process may be repeated as few or as many times as needed or desired to facilitate dislodgement.

Figure 5C:
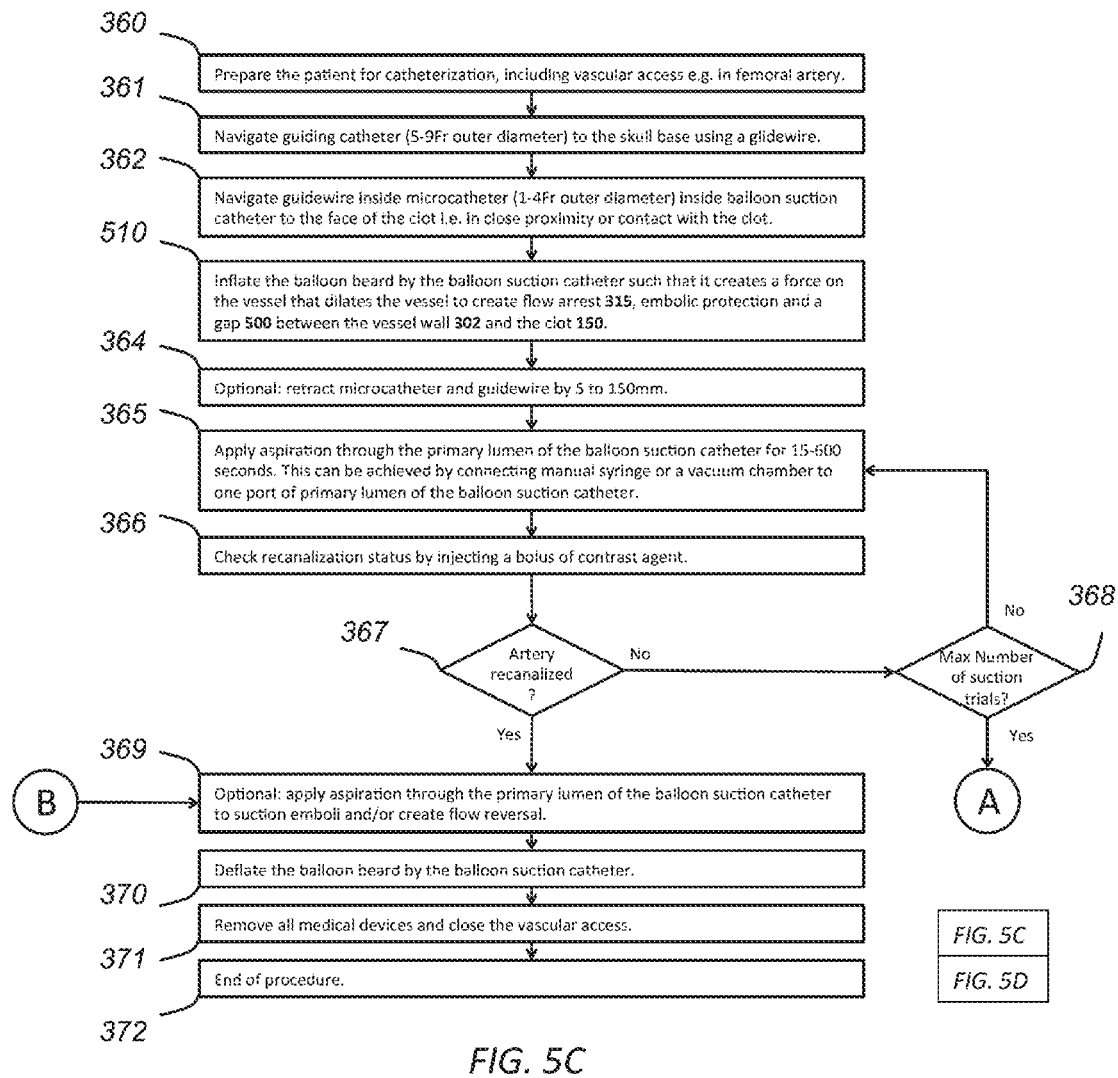
FIGS. 5C and 5D illustrate flow diagrams for using balloon inflation and artery dilation for facilitating dislodgement of the clot.
Figure 5D:
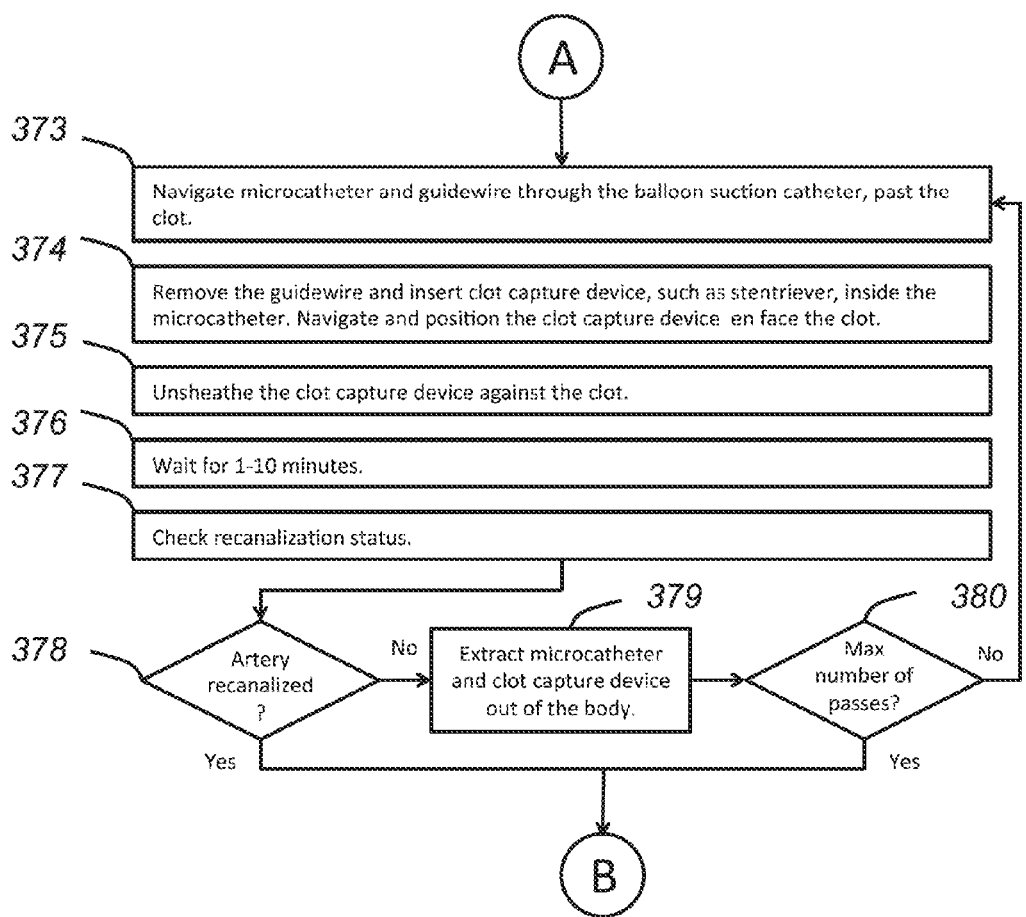

FIGS. 5C and 5D show a flow diagram illustrating details of the method for treating a clot within a vessel by providing suction, embolic protection, and flow reversal within the vessel similar to that shown in FIGS. 3F and 3G but with the addition of overinflating the balloon to facilitate clot dislodgement. In this variation, after the guidewire and catheter have been navigated into close proximity or contact with the clot per step 362, the additional step of overinflating the balloon may be performed per step 510. Accordingly, the balloon may be inflated such that it creates a force on the vessel that dilates the vessel to create flow arrest, embolic protection, and further creates the gap between the vessel wall and the clot. Then, the optional step of retracting the microcatheter and guidewire may be taken per step 364.

Figure 6A:
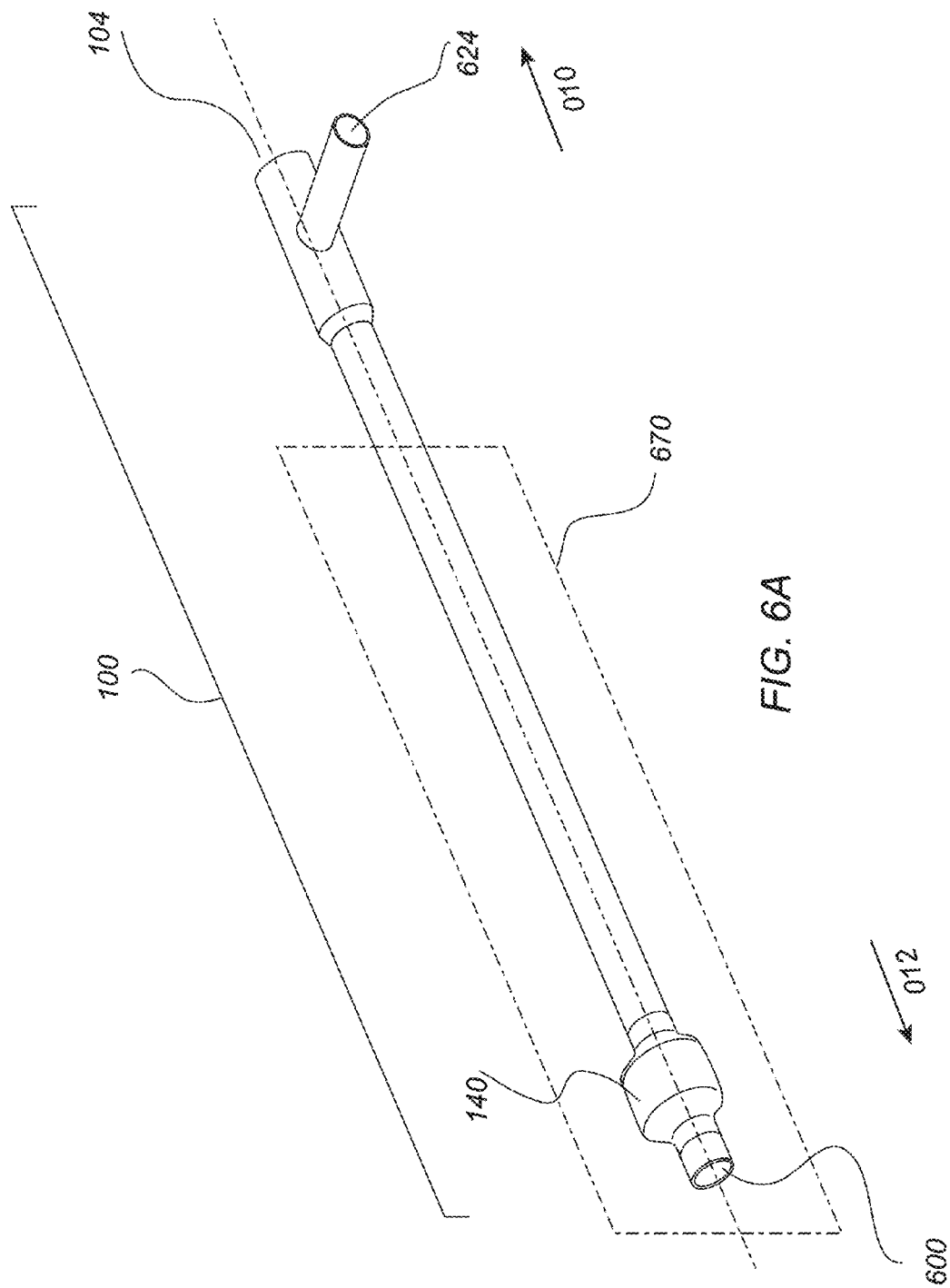
FIGS. 6A to 6C illustrate perspective and side views of one variation of a treatment catheter.
Figure 6B:
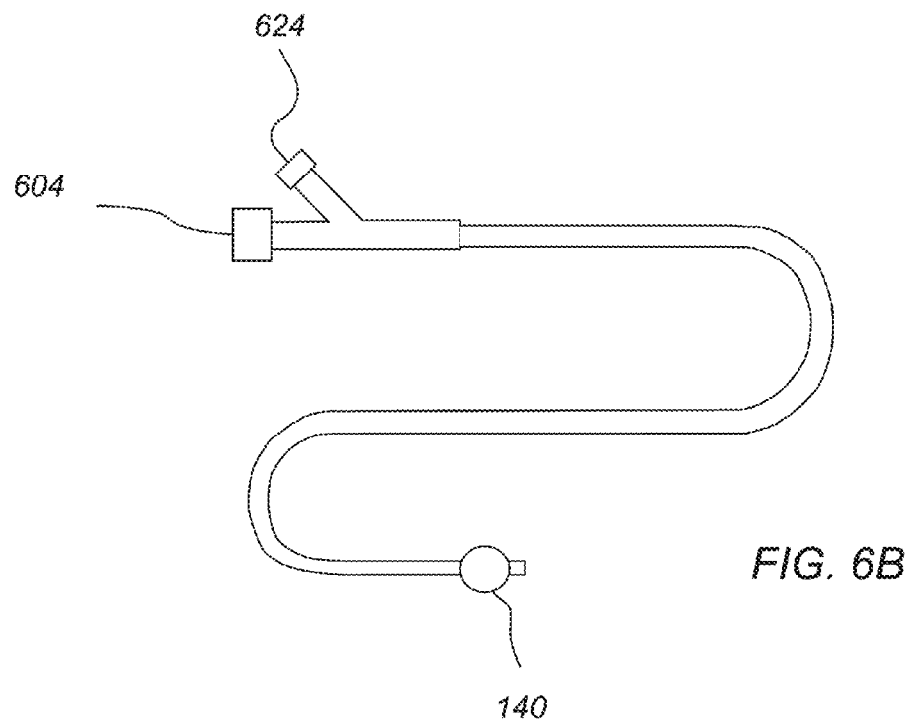
Figure 6C:
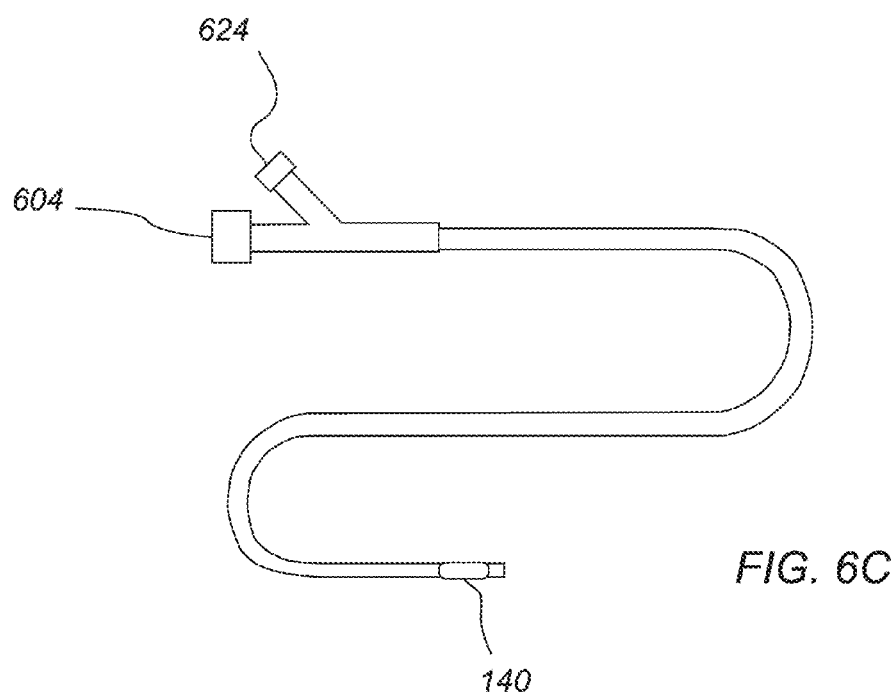

Turning now to the structure of the catheter 100, FIG. 6A shows a perspective view of one variation of the catheter body illustrating a primary lumen 600 which terminates in the distal opening for suctioning. The balloon 140 may be seen (in its inflated state) positioned upon or along an outer surface of the catheter body near or at the distal end of the catheter 100. The proximal end of the catheter body may be coupled to a hub 104 having one or more ports such as an inflation port 624 in fluid communication with the balloon 140 through a secondary inflation lumen which may have a diameter of between, e.g., 0.1 to 2 mm. FIGS. 6B and 6C illustrate respective side views of the catheter 100 showing examples of the balloon 140 in its inflated and deflected states. Any number of biocompatible such as saline, may be introduced into or removed through the inflation port 624 located at the proximal end of the catheter 100 to inflate and deflate the balloon 140 as shown.

In reference to cross-section 670 from FIG. 6A, FIGS. 7A and 7B show cross-sectional side views of variations of how the secondary inflation lumen may be fluidly coupled to the interior of the balloon 140. As illustrated in FIG. 7A, for instance, the wall 722 of the secondary lumen may be formed or otherwise attached to the external wall 702 of the primary lumen such that the secondary lumen 720 is formed externally of the primary lumen 600. The balloon 140 may accordingly be formed at least partially upon the external wall 702 of the primary lumen and over the external wall 722 of the secondary lumen (as shown by the proximal shaft interface 742 and distal shaft interface 744) such that the secondary lumen terminates within the interior of the balloon 140. The secondary lumen 720 may be fluidly coupled to the interior of the balloon 140, for instance, through one or more infusion openings 730, as shown, which provide a fluid path for the inflation fluid 732 to be evenly distributed within the balloon 140 interior. Alternatively, the secondary lumen 720 may terminate in a single opening within the balloon 140 interior, as shown in the cross-sectional view of FIG. 7B. These examples are not intended to be limiting but are shown for illustrative purposes of various configurations which may be utilized in combination with any of the features and methods described herein.

Turning now to the secondary inflation lumen 720, FIGS. 8A to 8F show cross-sectional end views of different configurations from the cross-sectional plane 780 of FIGS. 7A and 7B. FIG. 8A shows one variation where the secondary lumen 720 may be shaped in an arcuate configuration and formed within the wall 702 of the primary lumen 600. FIG. 8B illustrates another variation where the secondary lumen 720 may also be formed within the wall 702 of the primary lumen 600 but having a relatively narrower configuration.

FIG. 8C illustrates another variation where the secondary lumen 720 is formed partially upon the wall 702 of the primary lumen 600 surrounded by the external wall 722 of the secondary lumen such that the secondary lumen 720 has a curved rectilinear configuration. FIG. 8D shows another variation of the secondary lumen 720 formed as a separate arcuate lumen external to the wall 702 and FIG. 8E shows a similar configuration of secondary lumen 720 which is relatively narrower in width. FIG. 8F shows yet another variation where the secondary lumen 720 is shown as being formed external to the primary lumen 600 and also having a more circular cross-sectional configuration. These examples are also not intended to be limiting but are shown for illustrative purposes of various configurations which may be utilized in combination with any of the features and methods described herein.

Both the primary and secondary lumens may be reinforced by metallic braids, round-wire coils, flat-wire coils that may be embedded in the walls making up these lumens. The primary and secondary lumens may as well be lined (on their inner surface) with a thin material that displays a low friction coefficient with many materials, including polymeric and metallic materials, for example, Polytetrafluoroethylene (PTFE).

Figure 9A:
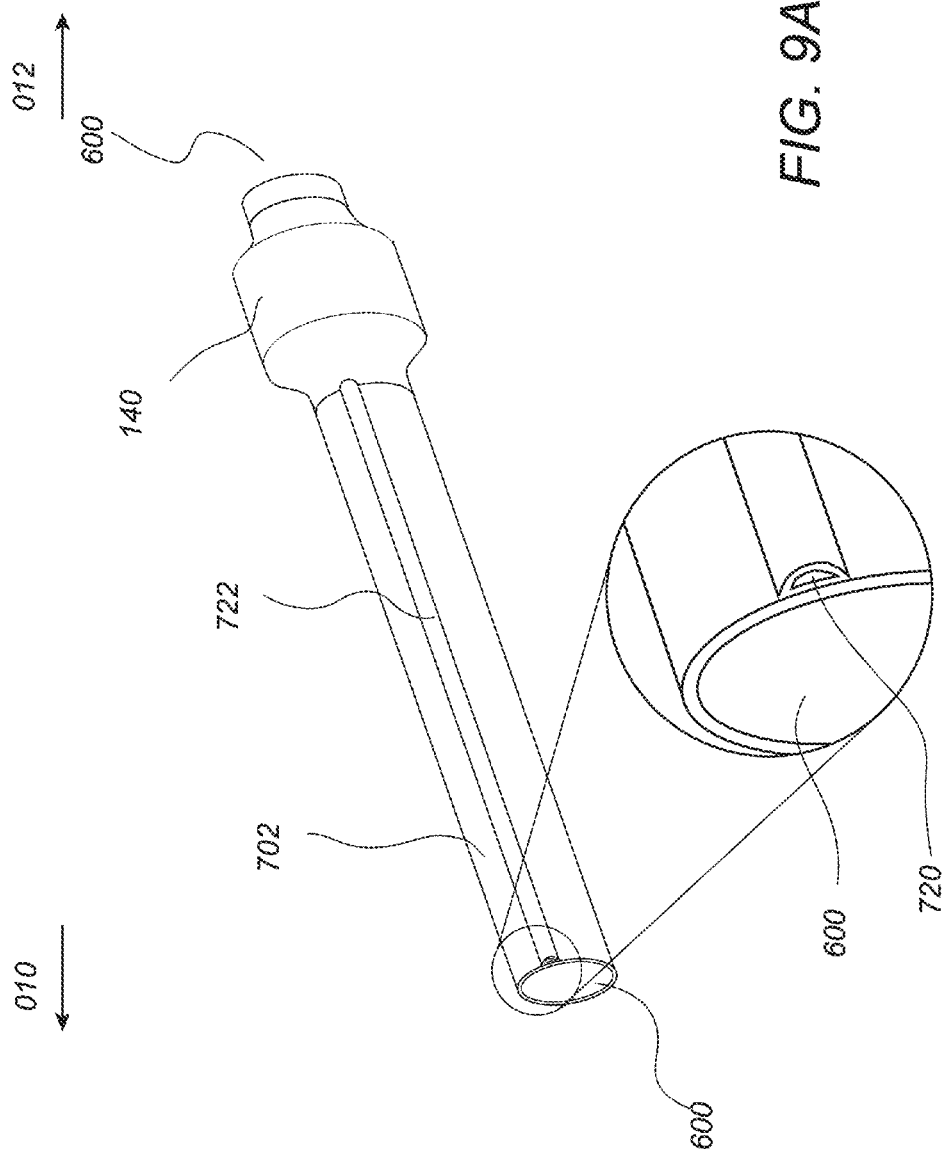
FIGS. 9A to 9D illustrate perspective views of different configurations that the secondary inflation lumen take over or along the external surface of the primary lumen.
Figure 9B:
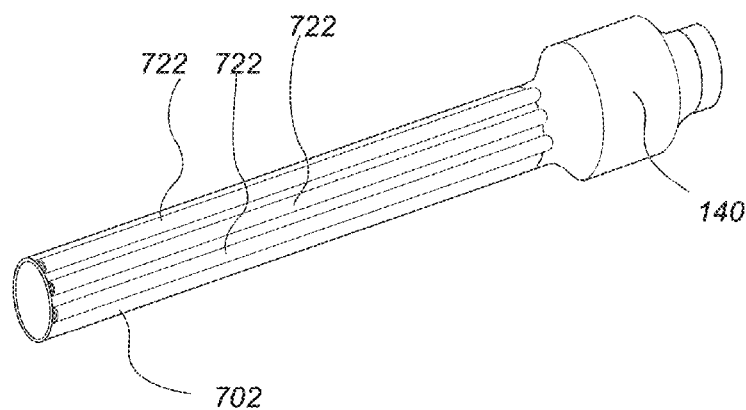
Figure 9C:
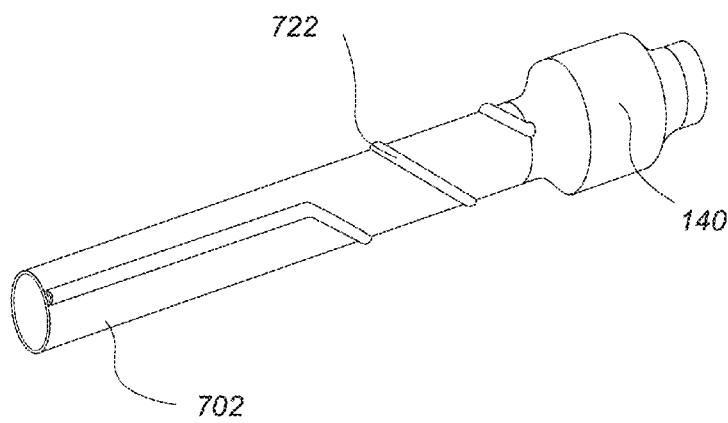
Figure 9D:
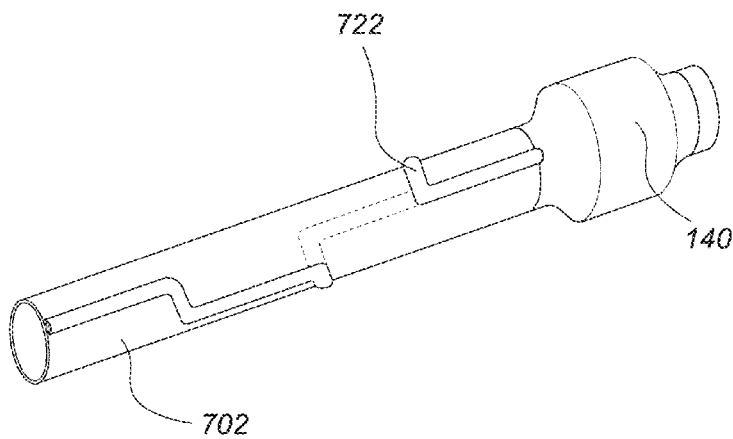

FIGS. 9A to 9D illustrate perspective views of some of the various layout configurations into which the secondary lumen 720 may be formed upon the external surface of the wall 702 of the primary lumen 600. FIG. 9A shows one variation where the secondary lumen 720 may be simply formed in a straightened configuration which follows in parallel the longitudinal axis of the primary lumen 600. FIG. 9B shows another variation where multiple secondary lumens may be aligned in parallel for fluid connection to the balloon 140. FIG. 9C shows yet another variation where the secondary lumen may be configured to follow along the wall 702 of the primary lumen in a helical configuration. This configuration, as well as the other configurations shown, may be incorporated along the last portion of the catheter, e.g., 2 to 15 inches, from the distal end of the catheter to facilitate the bending and tortuous shapes that the catheter 100 may undergo during use. FIG. 9D shows yet another variation where the secondary lumen may be configured to follow a path around the catheter external wall but where the secondary lumen forms parallel and transverse configurations relative to the longitudinal axis of the catheter 100. These and any of the secondary lumen configurations may be utilized in combination with any of the various features and methods described herein.

Figure 10A:
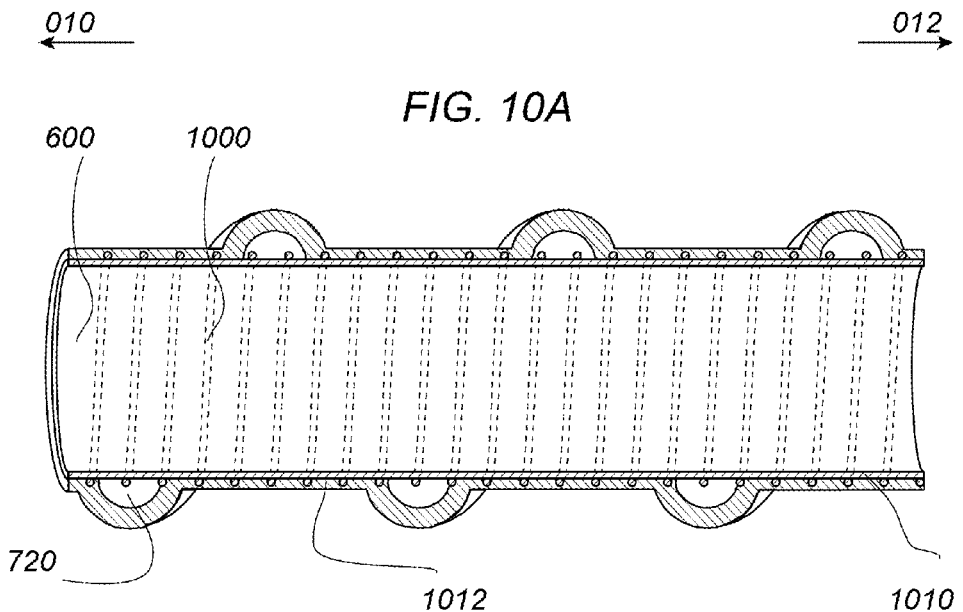
FIGS. 10A and 10B illustrate cross-sectional side views of another variation of the catheter structure.
Figure 10B:
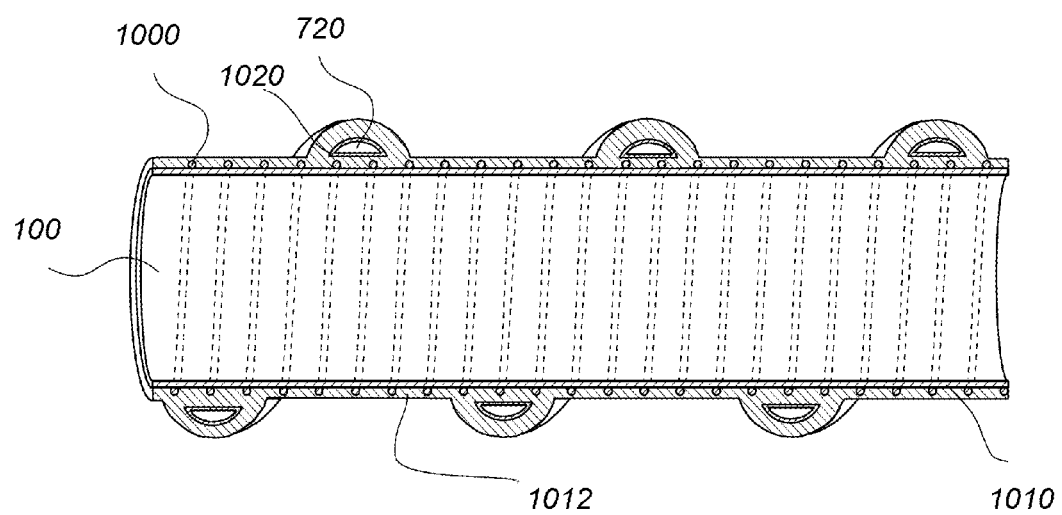

FIGS. 10A and 10B illustrate cross-sectional side views of the various configurations that the catheter 100 may be configured to provide for structural robustness while maintaining adequate flexibility for advancement within the cerebrovasculature. One variation is shown in FIG. 10A which illustrates a catheter 100 having a helical secondary lumen 720. The wall of the primary lumen 600 may be formed to have an inner liner 1010 (e.g., PTFE) with a reinforcement member 1000 which is configured as a coiled member wound helically around the inner liner 1010. An external jacket 1012 may be formed externally around both the reinforcement member 1000 and inner liner 1010. The external jacket 1012 may also form the externally positioned secondary lumen 720, as shown. FIG. 10B shows another variation where the secondary lumen 720 may also incorporate an inner liner 1020 (e.g., PTFE) which is helically positioned through the secondary lumen 720.

Figure 11A:
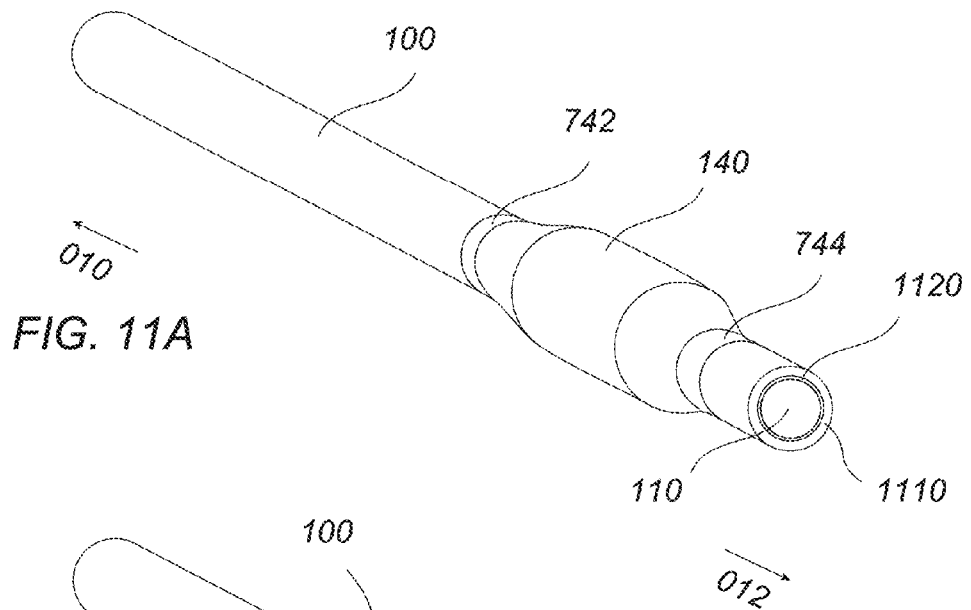
FIGS. 11A to 11C illustrate perspectives views of another variation of the catheter structure (with some elements removed for clarity purposes only) where both the primary and the secondary lumens are delimited by a liner and reinforced with coils.
Figure 11B:
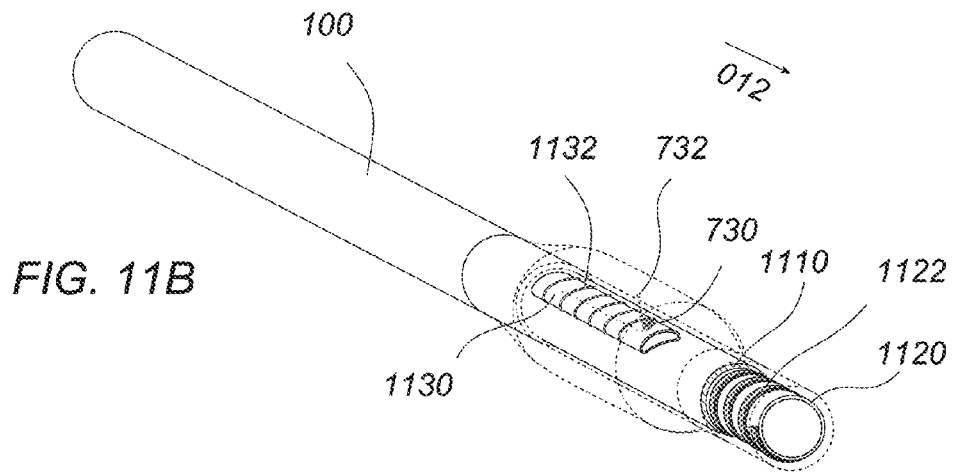
Figure 11C:
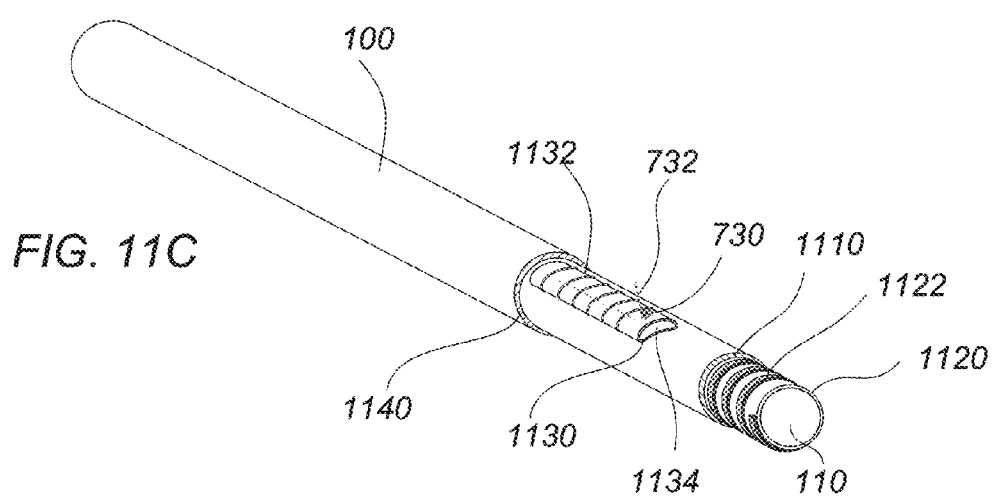

FIGS. 11A to 11C illustrate perspectives views of another variation of the catheter structure (with some elements removed for clarity purposes only) where both the primary and the secondary lumens are delimited by a liner and reinforced with coils. The variation of the catheter 100 may be seen in FIG. 11A as having balloon 140 in its inflated configuration. FIG. 11B shows a portion of the catheter removed for clarity purposes only and the balloon 140 shown in phantom. The primary lumen 110 is delimited by a liner 1120, e.g., a thin lubricious material such as PTFE, which is reinforced by a coil or braid 1122 wrapped helically around the liner 1120 and optionally covered by a polymeric jacket 1110.

The secondary lumen 1134, as shown in FIGS. 11B and 11C (which has the balloon removed for clarity purposes only) may also be delimited by a liner 1130 and reinforced by a coil or braids 1132 wrapped around the liner 1130. Another polymeric envelope 1140 can be used to cover both of the two primary and secondary lumens, liners, and coils. One or more holes or openings 730 may be pierced or otherwise formed through the secondary liner 1130, the coil 1132 and the outer jacket 1140 to allow for the fluid coupling of the secondary lumen 1134 to the interior of the balloon 140 to permit inflation and deflation. The coils and polymeric jackets may help to ensure the integrity of the secondary lumen 1134 and to keep it functional even though catheter 100 may be severely bent in the cerebrovasculature. The dashed arrow 732 indicates a possible path for the passage of fluid coming from the secondary lumen 1134 to inflate balloon 140.

These structural variations may be incorporated into any of the embodiments described herein and may also be utilized in any number of combinations with any of the features disclosed.

The applications of the devices and methods discussed above are not limited to applications within the cerebrovasculature but may include any number of further treatment applications such as those used in interventional cardiology, interventional peripheral radiology, interventional pulmonology and interventional nephrology. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method of treating a vessel, comprising:
    intravascularly advancing an elongate catheter through cerebrovasculature of a subject such that a distal opening of the elongate catheter is positioned in proximity to an obstruction located within the vessel;
    inflating a balloon positioned proximal to the distal opening along the elongate catheter into contact with a vessel wall such that a seal is formed between the balloon and the vessel wall;
    drawing a vacuum through a primary lumen of the elongate catheter such that a suction force is applied to the obstruction;
    further drawing the vacuum through the primary lumen until a flow of blood is reversed to flow proximally within the vessel and the obstruction is evacuated through primary lumen; and
    postconditioning by cycling the balloon between an inflated state and deflated state through at least two cycles to inhibit or prevent reperfusion injury to tissue surrounding the balloon.

2. The method of claim 1 wherein inflating a balloon comprises infusing a fluid through a secondary lumen defined along an exterior of the elongate catheter and in fluid communication with the balloon.

3. The method of claim 1 further comprising overinflating the balloon such that the vessel wall is distended and a force exerted by the vessel wall onto the obstruction is reduced such that a gap is formed between the vessel wall and the obstruction.

4. The method of claim 1 wherein further comprising positioning a microcatheter through the primary lumen and into contact with the obstruction prior to deflating the balloon until the flow of blood is reversed.

5. The method of claim 1 wherein postconditioning comprises waiting for a predetermined period of time between periods of balloon inflation.

6. The method of claim 1 wherein postconditioning comprises waiting for a predetermined period of time between periods of balloon deflation.

7. The method of claim 1 wherein postconditioning comprises cycling the balloon through 5 cycles of deflating the balloon for 30 seconds and then inflating the balloon for 30 seconds.

8. A method of treating ischemic stroke in a subject, comprising:
    positioning a distal opening of an elongate catheter to within 3 cm of a clot located within a neurovascular vessel;
    inflating a balloon positioned proximal to the distal opening along the elongate catheter into contact with a wall of the vessel such that a seal is formed between the balloon and the wall;
    drawing a vacuum through a primary lumen of the elongate catheter such that a suction force is applied to the clot;
    further drawing the vacuum through the primary lumen until a flow of blood is reversed to flow proximally within the vessel and the obstruction is evacuated through primary lumen; and
    postconditioning by cycling the balloon between an inflated state and a deflated state through at least two cycles to inhibit or prevent reperfusion injury to tissue surrounding the balloon.

9. The method of claim 8 wherein inflating a balloon comprises infusing a fluid through a secondary lumen defined along an exterior of the elongate catheter and in fluid communication with the balloon.

10. The method of claim 8 further comprising overinflating the balloon such that the vessel wall is distended and a force exerted by the vessel wall onto the obstruction is reduced such that a gap is formed between the vessel wall and the clot.

11. The method of claim 8 wherein further comprising positioning a microcatheter through the primary lumen and into contact with the clot prior to deflating the balloon until the flow of blood is reversed.

12. The method of claim 8 wherein postconditioning comprises waiting for a predetermined period of time between periods of balloon inflation.

13. The method of claim 8 wherein postconditioning comprises waiting for a predetermined period of time between periods of balloon deflation.

14. The method of claim 8 wherein postconditioning comprises cycling the balloon through 5 cycles of deflating the balloon for 30 seconds and then inflating the balloon for 30 seconds.

* * * * *